United States Patent
Snyder et al.

(10) Patent No.: US 9,898,656 B2
(45) Date of Patent: Feb. 20, 2018

(54) SYSTEMS AND METHODS FOR IDENTIFYING A CONTRA-ICTAL CONDITION IN A SUBJECT

(75) Inventors: David Snyder, Bainbridge Island, WA (US); Kent W. Leyde, Sammamish, WA (US); John F. Harris, Bellevue, WA (US)

(73) Assignee: Cyberonics, Inc., Houston, TX (US)

(*) Notice: Subject to any disclaimer, the term of this patent is extended or adjusted under 35 U.S.C. 154(b) by 1557 days.

(21) Appl. No.: 12/020,450

(22) Filed: Jan. 25, 2008

(65) Prior Publication Data

US 2008/0183096 A1    Jul. 31, 2008

Related U.S. Application Data

(60) Provisional application No. 60/897,549, filed on Jan. 25, 2007.

(51) Int. Cl.
| | |
|---|---|
| *A61B 5/04* | (2006.01) |
| *G06K 9/00* | (2006.01) |
| *A61B 5/0482* | (2006.01) |
| *A61B 5/0476* | (2006.01) |
| *G06F 19/00* | (2018.01) |

(Continued)

(52) U.S. Cl.
CPC ........ *G06K 9/00496* (2013.01); *A61B 5/0482* (2013.01); *A61B 5/4094* (2013.01); *G06F 19/3443* (2013.01); *A61B 5/0006* (2013.01); *A61B 5/0476* (2013.01); *G06F 19/24* (2013.01);

(Continued)

(58) Field of Classification Search
USPC ................................................. 600/544-545
See application file for complete search history.

(56) References Cited

U.S. PATENT DOCUMENTS

| | | | |
|---|---|---|---|
| 3,218,638 | A | 11/1965 | Honig |
| 3,498,287 | A | 3/1970 | Ertl |

(Continued)

FOREIGN PATENT DOCUMENTS

| | | |
|---|---|---|
| CA | 2251852 | 4/1999 |
| CA | 2423840 | 2/2002 |

(Continued)

OTHER PUBLICATIONS

Chen et al.; Clinical utility of video-EEG monitoring; Pediatric Neurology; vol. 12; No. 3; pp. 220-224; 1995.

(Continued)

*Primary Examiner* — Navin Natnithithadha
*Assistant Examiner* — Michael R Bloch
(74) *Attorney, Agent, or Firm* — Foley & Lardner LLP

(57) ABSTRACT

The invention provides a method of monitoring a subject's neurological condition. In some embodiments, the method includes the steps of analyzing a physiological signal (such as an EEG) from a subject to determine if the subject is in a contra-ictal condition; and if the subject is in a contra-ictal condition, providing an indication (e.g., to the subject and/or to a caregiver) that the subject is in the contra-ictal condition, such as by activating a green light or other visible output. In some embodiments, if the subject is in a pro-ictal condition, the method includes the step of providing an indication (such as a red light) that the subject is in the pro-ictal condition. The invention also provides neurological system monitors.

18 Claims, 13 Drawing Sheets

(51) Int. Cl.
*G06F 19/24* (2011.01)
*A61B 5/00* (2006.01)

(52) U.S. Cl.
CPC ............ *G06F 19/30* (2013.01); *G06F 19/345* (2013.01); *G06F 19/3418* (2013.01)

(56) References Cited

U.S. PATENT DOCUMENTS

| | | |
|---|---|---|
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,025,807 A | 6/1991 | Zabara |
| 5,031,618 A | 7/1991 | Mullett |
| 5,016,635 A | 12/1991 | Graupe |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deColriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |

(56) References Cited

U.S. PATENT DOCUMENTS

| | | |
|---|---|---|
| 5,782,874 A | 7/1998 | Loos |
| 5,782,891 A | 7/1998 | Hassler et al. |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,792,186 A | 11/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,938,689 A | 8/1999 | Fischell et al. |
| 5,941,106 A | 8/1999 | Barreras et al. |
| 5,941,906 A | 8/1999 | Barreras et al. |
| 5,950,632 A | 9/1999 | Reber et al. |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,208,893 B1 | 3/2001 | Hofmann |
| 6,221,011 B1 | 4/2001 | Bardy |
| 6,205,359 B1 | 5/2001 | Boveja |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,584 B2 | 6/2002 | Tziviskos et al. |
| 6,411,854 B1 | 6/2002 | Tziviskos et al. |
| 6,434,419 B1 | 8/2002 | Gevins et al. |
| 6,442,421 B1 | 8/2002 | Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,427,086 B1 | 11/2002 | Fischell et al. |
| 6,480,743 B1 | 11/2002 | Kirkpatrick |
| 6,484,132 B1 | 11/2002 | Hively et al. |
| 6,356,784 B1 | 12/2002 | Lozano et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,549,804 B1 | 4/2003 | Osorio et al. |
| 6,553,262 B1 | 4/2003 | Lang et al. |
| 6,547,746 B1 | 5/2003 | Marino |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,597,954 B1 | 7/2003 | Pless et al. |
| 6,600,956 B2 | 7/2003 | Maschino |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst et al. |
| 6,912,419 B2 | 6/2005 | Hill |
| 6,921,538 B2 | 7/2005 | Donovan |
| 6,921,541 B2 | 7/2005 | Chasin et al. |
| 6,901,292 B2 | 8/2005 | Whitehurst |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriquez |
| 6,973,342 B1 | 12/2005 | Swanson |
| 6,990,372 B2 | 1/2006 | Perron et al. |
| 7,010,351 B2 | 3/2006 | Firlik et al. |
| 7,089,059 B1 | 8/2006 | Pless |
| 7,117,108 B2 | 10/2006 | Rapp et al. |
| 7,174,212 B1 | 2/2007 | Klehn et al. |
| 7,177,701 B1 | 2/2007 | Pianca |
| 7,212,851 B2 | 5/2007 | Donoghue et al. |
| 7,231,254 B2 | 6/2007 | DiLorenzo |

(56) References Cited

U.S. PATENT DOCUMENTS

| | | |
|---|---|---|
| 7,324,851 B1 | 1/2008 | DiLorenzo |
| 7,373,198 B2 | 5/2008 | Bibian et al. |
| 7,463,917 B2 | 12/2008 | Martinez |
| 7,631,015 B2 | 12/2009 | Gupta et al. |
| 7,805,196 B2 | 9/2010 | Miesel et al. |
| 7,881,798 B2 | 2/2011 | Miesel et al. |
| 8,055,348 B2 | 11/2011 | Heruth et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1* | 8/2002 | Echauz et al. .................. 607/9 |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1* | 4/2004 | Echauz .................. A61B 5/0476 600/544 |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fishcell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1 | 1/2005 | Hall et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021108 A1 | 1/2005 | Klosterman et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1* | 5/2006 | Guttag et al. .................. 600/544 |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |

(56) References Cited

U.S. PATENT DOCUMENTS

| | | | |
|---|---|---|---|
| 2006/0293578 A1 | 12/2006 | Rennaker, II | |
| 2006/0293720 A1 | 12/2006 | DiLorenzo et al. | |
| 2007/0027367 A1 | 2/2007 | Oliver et al. | |
| 2007/0027514 A1 | 2/2007 | Gerber | |
| 2007/0035910 A1 | 2/2007 | Stevenson | |
| 2007/0043459 A1 | 2/2007 | Abbott, III et al. | |
| 2007/0055320 A1 | 3/2007 | Weinand | |
| 2007/0060973 A1 | 3/2007 | Ludvig et al. | |
| 2007/0073355 A1 | 3/2007 | DiLorenzo | |
| 2007/0073357 A1 | 3/2007 | Rooney et al. | |
| 2007/0100398 A1 | 5/2007 | Sloan | |
| 2007/0142862 A1 | 6/2007 | DiLorenzo | |
| 2007/0149952 A1 | 6/2007 | Bland et al. | |
| 2007/0150024 A1 | 6/2007 | Leyde et al. | |
| 2007/0150025 A1 | 6/2007 | DiLorenzo et al. | |
| 2007/0161919 A1 | 7/2007 | DiLorenzo | |
| 2007/0162086 A1 | 7/2007 | DiLorenzo | |
| 2007/0167991 A1 | 7/2007 | DiLorenzo | |
| 2007/0185890 A1 | 8/2007 | VanEpps et al. | |
| 2007/0197878 A1 | 8/2007 | Shklarski | |
| 2007/0213629 A1 | 9/2007 | Greene | |
| 2007/0213785 A1 | 9/2007 | Osorio et al. | |
| 2007/0217121 A1 | 9/2007 | Fu et al. | |
| 2007/0238939 A1 | 10/2007 | Giftakis et al. | |
| 2007/0244407 A1 | 10/2007 | Osorio | |
| 2007/0250077 A1 | 10/2007 | Skakoon et al. | |
| 2007/0250901 A1 | 10/2007 | McIntire et al. | |
| 2007/0287931 A1 | 12/2007 | DiLorenzo | |
| 2008/0021341 A1 | 1/2008 | Harris et al. | |
| 2008/0027347 A1 | 1/2008 | Harris et al. | |
| 2008/0027348 A1 | 1/2008 | Harris et al. | |
| 2008/0027515 A1 | 1/2008 | Harris et al. | |
| 2008/0033502 A1 | 2/2008 | Harris et al. | |
| 2008/0082019 A1 | 4/2008 | Ludving et al. | |
| 2008/0091090 A1 | 4/2008 | Guillory et al. | |
| 2008/0103556 A1 | 5/2008 | Li et al. | |
| 2008/0161712 A1 | 7/2008 | Leyde | |
| 2008/0161713 A1 | 7/2008 | Leyde et al. | |
| 2008/0221876 A1 | 9/2008 | Holdrich | |
| 2008/0273287 A1 | 11/2008 | Iyer et al. | |
| 2008/0319281 A1 | 12/2008 | Aarts | |
| 2009/0062696 A1 | 3/2009 | Nathan et al. | |
| 2009/0264952 A1 | 10/2009 | Jassemidis et al. | |
| 2010/0023089 A1 | 1/2010 | DiLorenzo | |
| 2010/0292602 A1 | 11/2010 | Worrell et al. | |
| 2011/0260855 A1 | 10/2011 | John et al. | |
| 2011/0319785 A1 | 12/2011 | Snyder et al. | |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022 | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 04/008373 A2 | 1/2004 |
| WO | WO 04/032720 A2 | 4/2004 |
| WO | WO 04/034231 A2 | 4/2004 |
| WO | WO 04/034879 A2 | 4/2004 |
| WO | WO 04/034880 A2 | 4/2004 |
| WO | WO 04/034881 A2 | 4/2004 |
| WO | WO 04/034882 A2 | 4/2004 |
| WO | WO 04/034883 A2 | 4/2004 |
| WO | WO 04/034885 A2 | 4/2004 |
| WO | WO 04/034982 A2 | 4/2004 |
| WO | WO 04/034997 A2 | 4/2004 |
| WO | WO 04/034998 A2 | 4/2004 |
| WO | WO 04/035130 A2 | 4/2004 |
| WO | WO 04/036370 A2 | 4/2004 |
| WO | WO 04/036372 A2 | 4/2004 |
| WO | WO 04/036376 A2 | 4/2004 |
| WO | WO 04/036377 A2 | 4/2004 |
| WO | WO 04/037342 A2 | 5/2004 |
| WO | WO 04/043536 A1 | 5/2004 |
| WO | WO 04/091718 A1 | 10/2004 |
| WO | WO 05/007236 A2 | 1/2005 |
| WO | WO 05/028026 A1 | 3/2005 |
| WO | WO 05/028028 A1 | 3/2005 |
| WO | WO 05/031630 A2 | 4/2005 |
| WO | WO 05/051167 A1 | 6/2005 |
| WO | WO 05/051306 A2 | 6/2005 |
| WO | WO 05/117693 A1 | 12/2005 |
| WO | WO 06/014971 A2 | 2/2006 |
| WO | WO 06/014972 A2 | 2/2006 |
| WO | WO 2006/020794 A2 | 2/2006 |
| WO | WO 2006/035392 A1 | 4/2006 |
| WO | WO 07/150003 A2 | 12/2007 |

OTHER PUBLICATIONS

Snyder et al; The statistics of a practical seizure warning system; Journal of Neural Engineering; vol. 5; pp. 392-401; 2008.

(56) References Cited

OTHER PUBLICATIONS

DiLorenzo, Daniel; U.S. Appl. No. 12/177,060 entitled "Closed-loop feedback-driven neuromodulation," filed Jul. 21, 2008.
Bland et al.; U.S. Appl. No. 12/180,996 entitled "Patient advisory device," filed Jul. 28, 2008.
Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.
Franaszczuk et al.; An autoregressive method for the measurement of synchronization of interictal and ictal EEG signals; Biological Cybernetics, vol. 81; No. 1; pp. 3-9; 1999.
Mormann et al.; Seizure prediction: the long and winding road; Brain; vol. 130; No. 2; pp. 314-333; Sep. 28, 2006.
Sackellares et al.; Predictability analysis for an automated seizure prediction algorithm; Journal of Clinical Neurophysiology; vol. 23; No. 6; pp. 509-520; Dec. 2006.
Schelter et al.; Testing statistical significance of multivariate time series analysis techniques for epileptic seizure prediction; Chaos: An Interdisciplinary Journal of Nonlinear Science; vol. 16; No. 013108; pp. 1-10; Jan. 2006.
Wong et al.; A stochastic framework for evaluating seizure prediction algorithms using hiden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.
Himes, David M.; U.S. Appl. No. 12/630,300 entitled "Universal Electrode Array for Monitoring Brain Activity," filed Dec. 3, 2009.
Himes et al.; U.S. Appl. No. 12/646,783 entitled "Brain State Analysis Based on Select Seizure Onset Characteristics and Clinical Manifestations," filed Dec. 23, 2009.
Echauz et al.; U.S. Appl. No. 12/649,098 entitled "Processing for Multi-Channel Signals," filed Dec. 29, 2009.
Floyd et al.; U.S. Appl. No. 12/685,543 entitled "Medical Lead Termination Sleeve for Implantable Medical Devices," filed Jan. 11, 2010.
Harris et al.; U.S. Appl. No. 12/691,650 entitled "Minimally invasive system for selecting patient-specific therapy parameters," filed Jan. 21, 2010.
Rimes et al.; U.S. Appl. No. 12/716,132 entitled "Displaying and Manipulating Brain Function Data Including Enhanced Data Scrolling Functionality," filed Mar. 2, 2010.
Himes et al.; U.S. Appl. No. 12/716,147 entitled "Displaying and Manipulating Brain Function Data Including Filtering of Annotations," filed Mar. 2, 2010.
Rothman et al.; Local Cooling: a therapy for intractable neocortical epilepsy; Epilepsy Currents; vol. 3; No. 5; pp. 153-156; Sep./Oct. 2003.
Higgins et al.; U.S. Appl. No. 13/026,961 entitled "Neurological monitoring and alerts," filed Feb. 14, 2011.
Harris et al.; U.S. Appl. No. 13/050,839 entitled "System and methods for analyzing seizure activity," filed Mar. 17, 2011.
Leyde et al.; U.S. Appl. No. 13/070,333 entitled "Communication Error Alerting in an Epilepsy Monitoring System," filed Mar. 23, 2011.
Leyde et al.; U.S. Appl. No. 13/070,357 entitled "Patient Entry Recording in an Epilepsy Monitoring System," filed Mar. 23, 2011.
DiLorenzo, Daniel; U.S. Appl. No. 12/774,550 entitled "Systems for Monitoring a Patient's Neurological Disease State," filed May 5, 2010.
Echauz et al.; U.S. Appl. No. 12/792,582 entitled "Processing for Multi-Channel Signals," filed Jun. 2, 2010.
Snyder et al.; U.S. Appl. No. 12/053,312 entitled "Implantable systems and methods for identifying a contra-ictal condition in a subject," filed Mar. 21, 2008.
Leyde et al.; U.S. Appl. No. 13/441,609 entitled "Multi-Channel Amplifier Techniques," filed Apr. 6, 2012.
DiLorenzo et al.; U.S. Appl. No. 13/439,531 entitled "Extracranial Monitoring of Brain Activity," filed Apr. 4, 2012.
Spector et al.; High and Low Perceived Self-Control of Epileptic Seizures; Epilepsia, vol. 42(4), Apr. 2001; pp. 556-564.
DiLorenzo, Daniel, U.S. Appl. No. 11/743,607, entitled "Controlling a Subject's Susceptibility to a Seizure," filed May 2, 2007.
DiLorenzo, Daniel, U.S. Appl. No. 11/743,611, entitled "Providing Output Indicative of Subject's Disease State," filed May 2, 2007.
DiLorenzo, Daniel, U.S. Appl. No. 11/282,317 entitled "Closed-loop vag nerve stimulation," filed Nov. 17, 2005.
Harris, John, U.S. Appl. No. 11/734,190, entitled "Methods and Template Assembly for Implanting an Electrode Array in a Patient," filed Apr. 11, 2007.
Leyde, Kent; U.S. Appl. No. 11/599,179, entitled "Systems and methods of reducing artifact in neurological stimulation systems," filed Nov. 14, 2006.
Leyde et al.; U.S. Appl. No. 12/020,507 entitled "Methods and systems for measuring a subject's susceptibility to a seizure," filed Jan. 25, 2008.
Snyder et al.; U.S. Appl. No. 12/035,335 entitled "Methods and systems for characterizing and generating a patient-specific seizure prediction system," filed Feb. 21, 2008.
Adjouadi, et al. A new mathematical approach based on orthogonal operators for the detection of interictal spikes in epileptogenic data. Biomed. Sci. Instrum. 2004; 40: 175-80.
Adjouadi, et al. Detection of interictal spikes and artifactual data through orthogonal transformations. J. Clin. Neurophysiol. 2005; 22(1):53-64.
Adjouadi, et al. Interictal spike detection using the Walsh transform. IEEE Trans. Biomed. Eng. 2004; 51(5): 868-72.
Aksenova, et al. Nonparametric on-line detection of changes in signal spectral characteristics for early prediction of epilepsy seizure onset. J. Automation and Information Sciences. 2004; 36(8): 35-45.
Aksenova, et al. On-line disharmony detection for early prediction of epilepsy seizure onset. 5th International Workshop Neural Coding 2003. Aulla (Italy) Sep. 20-25, 2003. (Abstract).
Andrzejak, et al. Bivariate surrogate techniques: necessity, strengths, and caveats. Physical Review E. 2003; 68: 066202-1-066202-15.
Andrzejak, et al. Testing the null hypothesis of the nonexistence of a preseizure state. Physical Review E. 2003; 67: 010901-1-010901-4.
Aschenbrenner-Scheibe, et al. How well can epileptic seizures be predicted? An evaluation of a nonlinear method. Brain. 2003; 126: 2616-26.
Bangham et al. Diffusion of univalent ions across the lamellae of swollen phospholipids. 1965. J Mol. Biol. 13: 238-252.
Baruchi, et al. Functional holography of complex networks activity—From cultures to the human brain. Complexity. 2005; 10(3): 38 R 51.
Baruchi, et al. Functional holography of recorded neuronal networks activity. Neuroinformatics. 2004; 2(3): 333-51.
Ben-Hur, et al. Detecting stable clusters using principal component analysis. Methods Mol. Biol. 2003; 224: 159-82.
Bergey, et al. Epileptic seizures are characterized by changing signal complexity. Clin. Neurophysiol. 2001; 112(2): 241-9.
Betterton, et al. Determining State of Consciousness from the Intracranial Electroencephalogram (IEEG) for Seizure Prediction. From Proceeding (377) Modeling, Identification, and Control. 2003; 377-201: 313-317.
Bhattacharya, et al. Enhanced phase synchrony in the electroencephalograph gamma band for musicians while listening to music. Phys. Rev. E. 2001; 64:012902-1-4.
Boley, et al. Training Support Vector Machine using Adaptive Clustering. 2004 SIAM International Conference on Data Mining, Apr. 22-Apr. 24, 2004. Lake Buena Vista, FL, USA. 12 pages.
Burges, C. A Tutorial on Support Vector Machines for Pattern Recognition. Data Mining and Knowledge Discovery. 1998; 2: 121-167.
Cao, et al. Detecting dynamical changes in time series using the permutation entropy. Physical Review E. 2004; 70:046217-1-046217-7.

(56) References Cited

OTHER PUBLICATIONS

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

D'Alessandro, et al. A multi-feature and multi-channel univariate selection process for seizure prediction. Clin. Neurophysiol. 2005; 116(3): 506-16.

Drury, et al. Seizure prediction using scalp electroencephalogram. Exp. Neurol. 2003; 184 Suppl 1: S9-18.

Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, a report of the therapeutics and technology assessment subcommittee of the American Academy of Neurology. Neurology.53: 666-669.

Gardner, A. B. A Novelty Detection Approach to Seizure Analysis from Intracranial EEG. Georgia Institute of Technology. Apr. 2004. A dissertation available at http://etd.gatech.edu/theses /available/ etd-04122004-132404 /unrestricted/gardner_andrew_b_200405_ phd.pdf Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/ hively/NBICradaAnnualRpt FY00.pdf. Accessed Feb. 28, 2006.

Hjorth, B. Source derivation simplifies topographical EEG interpretation. Am. J. EEG Technol. 1980; 20: 121-132.

Hsu, et al. A practical guide to support vector classification. Technical report, Department of Computer Science and Information Technology, National Taiwan University, 2003. Available at http:// www.csie.ntu.edu.tw/~cjlin/papers/guide/guide.pdf. Accessed Feb. 28, 2006.

Huynh, J. A. Evaluation of Gene Selection Using Support Vector Machine Recursive Feature Elimination. Arizona State University. May 26, 2004. (28 pages).

Huynh, J. A. Evaluation of Gene Selection Using Support Vector Machine Recursive Feature Elimination. Presentation slides. (41 pages) (May 26, 2004).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. The Neuroscientist. 1996; 2:118-126.

Iasemidis, et al. Comment on "Inability of Lyapunov exponents to predict epileptic seizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focwith Extrafocal Sites in Temporal Lobe Epilepsy (TLE). Ann. Neurol. 1997; 42, pp. 429. pp. M146.

Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-64.

Iasemidis, et al. Long-term prospective on-line real-time seizure prediction. Clin. Neurophysiol. 2005; 116 (3):532-44.

Iasemidis, et al. Long-Time-Scale Temporo-spatial Patterns of Entrainment of Preictal Electrocorticographic Data in Human Temporal Lobe Epilepsy. Epilepsia. 1990; 31(5):621.

(56) References Cited

OTHER PUBLICATIONS

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Vers Postictal Analysis for Epileptogenic Foc Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4):657-663.
Katz, et al. Does interictal spiking change prior to seizures? Electroencephalogr. Clin. Neurophysiol. 1991; 79 (2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326 (9):787-840.
Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.
Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physica D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: its possible use for interictal foc localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.
Lehnertz, et al. The First International Collaborative Workshop on Seizure Prediction: summary and data description. Clin. Neurophysiol. 2005; 116(3):493-505.
Lehnertz, K. Non-linear time series analysis of intracranial EEG recordings in patients with epilepsy—an overview. Int. J. Psychophysiol. 1999; 34(1):45-52.
Lemos, et al. The weighted average reference montage. Electroencephalogr. Clin. Neurophysiol. 1991; 79 (5):361-70.
Li, et al. Fractal spectral analysis of pre-epileptic seizures in terms of criticality. J. Neural Eng. 2005; 2(2):11-16.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186 (1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by a linear and a nonlinear method. IEEE Trans. Biomed. Eng. 2003; 50(5):628-33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate after discharges. Clin. Neurophysiol. 2002; 113(1):33-42.

(56) References Cited

OTHER PUBLICATIONS

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53 (3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19 (2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57 (2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18 (3):223-45.

Rahimi, et al. On the Effectiveness of Aluminum Foil Helmets: An Empirical Study. Available at http://people.csail.mit.edu/rahimi/helmet/. Accessed Mar. 2, 2006.

Robinson, et al. Steady States and Global Dynamics of Electrical Activity in the Cerebral Cortex. Phys. Rev. E. 1998; (58):3557-3571.

Rudrauf, et al. Frequency flows and the time-frequency dynamics of multivariate phase synchronization in brain signals. NeuroImage. 2005. (19 pages.).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989; 30(5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

Sackellares, J. C. Epilepsy—when chaos fails. In: chaos in the brain? Eds. K. Lehnertz & C.E. Eiger. World Scientific. 2000 (22 pages).

Salant, et al. Prediction of epileptic seizures from two-channel EEG. Med. Biol. Eng. Comput. 1998; 36 (5):549-56.

Schelter, et al. Testing for directed influences among neural signals using partial directed coherence. J. Neurosci. Methods. 2006; 152(1-2):210-9.

Schindler, et al. EEG analysis with simulated neuronal cell models helps to detect pre-seizure changes. Clin. Neurophysiol. 2002; 113(4):604-14.

Schwartzkroin, P. Origins of the Epileptic State. Epilepsia. 1997; 38, supply. 8, pp. 853-858.

Sheridan, T. Humans and Automation. NY: John Wiley. 2002.

Shoeb et al. Patient-specific seizure detection. MIT Computer Science and Artificial Intelligence Laboratory. 2004; pp. 193-194.

Staba, et al. Quantitative analysis of high-frequency oscillations (80-500 Hz) recorded in human epileptic hippocampand entorhinal cortex. J. Neurophysiol. 2002; 88(4):1743-52.

Stefanski, et al. Using chaos synchronization to estimate the largest Lyapunov exponent of nonsmooth systems. Discrete Dynamics in Nature and Society. 2000; 4:207-215.

Subasi, et al. Classification of EEG signals using neural network and logistic regression. Computer Methods Programs Biomed. 2005; 78(2):87-99.

Szoka et al. Procedure for preparation of liposomes with large internal aqueospace and high capture volume by reverse phase evaporation. 1978. Proc. Natl Acad. Sci. USA. 75: 4194-4198.

Tass, et al. Detection of n: m Phase Locking from Noisy Data: Application to Magnetoencephalography. Physical Review Letters. 1998; 81(15):3291-3294.

Terry, et al. An improved algorithm for the detection of dynamical interdependence in bivariate time-series. Biol. Cybern. 2003; 88(2):129-36.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to assess and compare seizure prediction methods. Epilepsy Behav. 2003; 4(3):318-25.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T. B. Ho, D. Cheung, and H. Liu (Eds.): PAKDD. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518R1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114 (10):1963-73.

Tetzlaff, et al. Cellular neural networks (CNN) with linear weight functions for a prediction of epileptic seizures. Int'l. J. of Neural Systems. 2003; 13(6):489-498.

Theiler, et al. Testing for non-linearity in time series: the method of surrogate data. Physica D. 1992; 58:77-94.

(56) References Cited

OTHER PUBLICATIONS

Tsakalis, K. S. Prediction and control of epileptic seizures: Coupled oscillator models. Arizona State University. (Slide: 53 pages) (No date).

Van Drongelen, et al, Seizure anticipation in pediatric epilepsy: use of Kolmogorov entropy. Pediatr. Neurol. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neurol. 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

\* cited by examiner

| | Pro-ictal | Contra-ictal | Output to Patient |
|---|---|---|---|
| 52 → | L | L | Yellow |
| 54 → | L | H | Green |
| 56 → | H | H | Yellow |
| 58 → | H | L | Red |

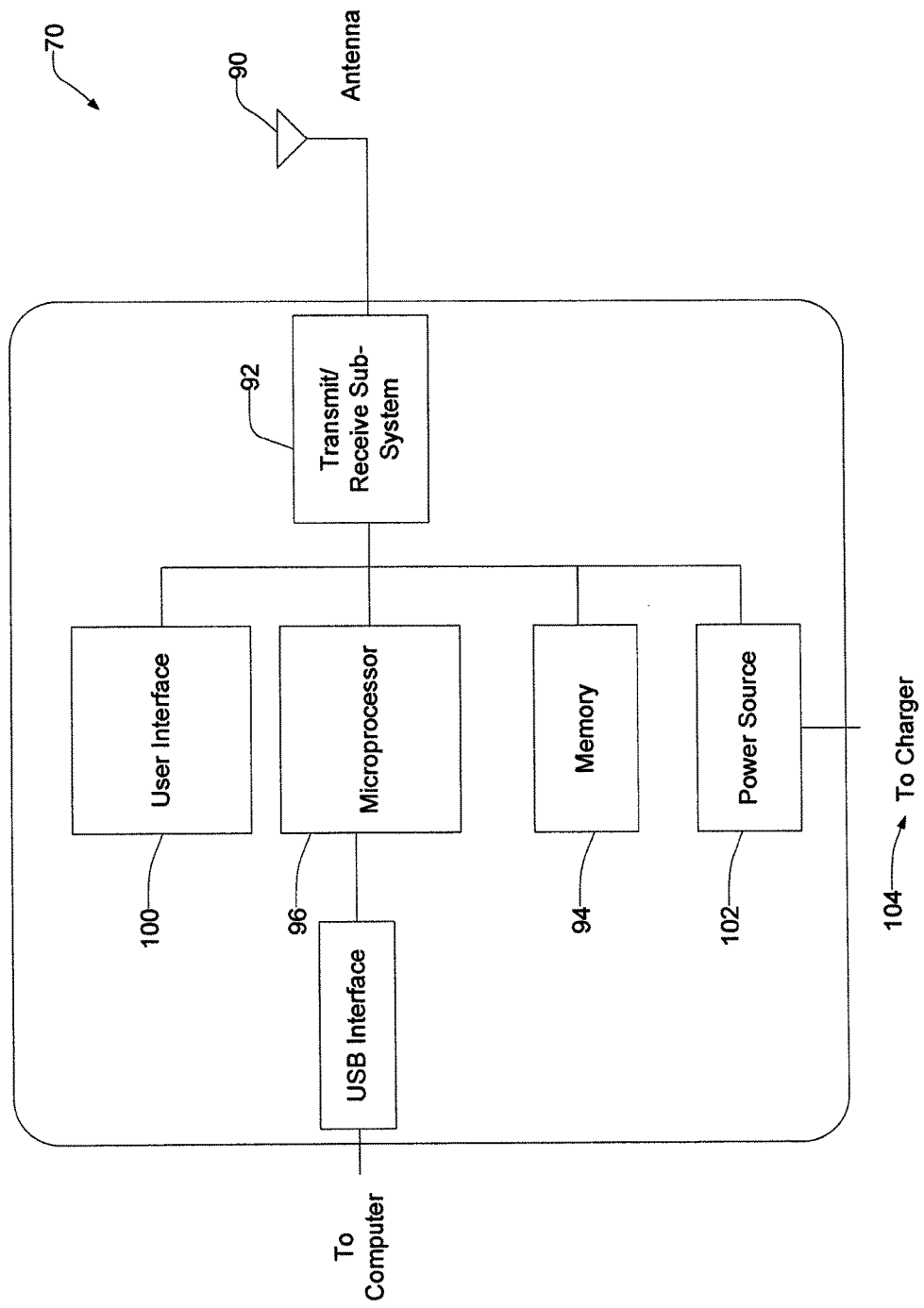

SYSTEMS AND METHODS FOR IDENTIFYING A CONTRA-ICTAL CONDITION IN A SUBJECT

CROSS-REFERENCE TO RELATED APPLICATIONS

The present application claims benefit of U.S. Provisional Patent Application No. 60/897,549, filed Jan. 25, 2007, to Snyder et al., entitled "Systems and Methods for Identifying a Contra-ictal Condition in a Subject," the disclosure of which is incorporated by reference herein in its entirety.

BACKGROUND OF THE INVENTION

The present invention relates generally to systems and methods for monitoring a subject's neurological condition. More specifically, the present invention is related to methods and systems for monitoring a subject who has epilepsy and determining if the subject is in a contra-ictal condition in which the subject is at low susceptibility for a seizure and is unlikely to transition into a pre-seizure condition within a computed or predetermined time period.

Epilepsy is a disorder of the brain characterized by chronic, recurring seizures. Seizures are a result of uncontrolled discharges of electrical activity in the brain. A seizure typically manifests as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of subjects. People with uncontrolled epilepsy are often significantly limited in their ability to work in many industries and cannot legally drive an automobile. An uncommon, but potentially lethal form of seizure is called status epilepticus, in which a seizure continues for more than 30 minutes. This continuous seizure activity may lead to permanent brain damage, and can be lethal if untreated.

While the exact cause of epilepsy is uncertain, epilepsy can result from head trauma (such as from a car accident or a fall), infection (such as meningitis), or from neoplastic, vascular or developmental abnormalities of the brain. Most epilepsy, especially most forms that are resistant to treatment (i.e., refractory), is idiopathic or of unknown causes, and is generally presumed to be an inherited genetic disorder. Demographic studies have estimated the prevalence of epilepsy at approximately 1% of the population, or roughly 2.5 million individuals in the United States alone. Approximately 60% of these subjects have focal epilepsy where a defined point of onset can be identified in the brain and are therefore candidates for some form of a focal treatment approach.

If it is assumed that an "average" subject with focal epilepsy has between 3 and 4 seizures per month, in which each of the seizures last for several seconds or minutes, the cumulative time the subject would be seizing is only about one hour per year. The other 99.98% of the year, the epileptic subject is free from seizures. The debilitating aspect of epilepsy is the constant uncertainty of when the next seizure is going to strike. It is this constant state of uncertainty which causes epileptic subjects to remove themselves from society. It is the constant fear and uncertainty of when the next seizure will strike that prevents the person from performing activities that most non-epileptic subjects take for granted.

To that end, there have been a number of proposals from groups around the world for predicting seizures and warning the subject of the impending seizure. Most of such proposals attempt to analyze the subject's electroencephalogram or electrocorticograms (referred to collectively as "EEGs"), to differentiate between a "pre-ictal condition" (i.e., pre-seizure condition) and an "inter-ictal condition" (i.e., between seizures). To date, however, none of the proposed systems have proven to be effective in predicting seizures. Some researchers have proposed that seizures develop minutes to hours before the clinical onset of the seizure. These researchers therefore classify the pre-ictal condition as the beginning of the ictal or seizure event which begins with a cascade of events. Under this definition, a seizure is imminent and will occur if a pre-ictal condition is observed. Others believe that a pre-ictal condition represents a state which only has a high susceptibility for a seizure and does not always lead to a seizure and that seizures occur either due to chance (e.g., noise) or via a triggering event during this high susceptibility time period. For clarity, the term "pro-ictal" is introduced here to represent a state or condition that represents a high susceptibility for seizure; in other words, a seizure can happen at any time. Ictal activity, within the scope of epilepsy, refers to seizure activity. Ictal activity may have other meanings in other contexts.

SUMMARY OF THE INVENTION

Prior art seizure detection and warning systems focused only on the identification of ictal or pro-ictal physiological data from the patient. See, e.g., Litt U.S. Pat. No. 6,658,287. While being able to determine that the subject is in a "pro-ictal" condition is highly desirable, identifying when the subject has entered or is likely to enter a pro-ictal condition is only part of the solution for these subjects. An equally important aspect of any seizure advisory system is the ability to be able to inform the subject when they are unlikely to have a seizure for a predetermined period of time (e.g., low susceptibility or "contra-ictal"). Simply knowing that the subject is not pro-ictal does not provide the subject with the assurance that they will not quickly transition into a pro-ictal or ictal condition. Knowing that they are in a contra-ictal state can allow the subject to engage in normal daily activities, such as driving a car, or walking down a set of stairs, without fearing that they will have a seizure. Knowing when a seizure is unlikely to occur can be even more important for the subject's sense of freedom than being alerted when a seizure it likely to occur.

Furthermore, for one reason or another, it may not be possible to accurately predict the seizures in a portion of the subject population. However, for that same portion of the subject population, it may be possible to let the subject know when they are unlikely to have a seizure for a period of time.

Therefore what are needed are methods and systems that are able to inform the subject that they are highly unlikely to transition into a pro-ictal or ictal condition in a period of time. It would further be desirable if such systems and methods could substantially continuously provide an output to the subject to differentiate when the subject is at a low susceptibility to seizure, raised susceptibility to seizure, and/or a high susceptibility to seizure.

One aspect of the invention provides a method for identifying a contra-ictal condition for a subject. In some embodiments, the method includes the step of obtaining a physiological signal dataset (such as EEG data) from the subject; generating an N-dimensional feature vector for different time points of the physiological signal dataset; identifying a grouping of feature vectors or a region of an N-dimensional feature space that is substantially free from ictal activity (such as a seizure and/or pro-ictal activity) and is separated in time from subsequent ictal activity by a computed or predetermined time period; and using the grouping of feature vectors or region of the N-dimensional feature space to identify a contra-ictal condition of the subject. In some embodiments, the method includes the step of storing the identified grouping of feature vectors or a mathematical representation of the identified grouping of feature vectors in memory. The invention may also include the step of customizing a contra-ictal algorithm for the subject based on the N-dimensional feature vector and disposing the contra-ictal algorithm in a physiological signal monitoring device.

Another aspect of the invention provides a method of developing a physiological signal monitoring algorithm. In some embodiments, the method includes the steps of: obtaining a physiological signal (such as an EEG) from a subject; identifying ictal activity in the physiological signal; extracting N features from the physiological signal; generating a feature vector of the extracted N features for time points of the physiological signal; identifying a grouping of points in a feature space that is free from ictal activity (such as a seizure and/or pro-ictal activity) and is separated in time from the ictal activity by a predetermined or computed time period, wherein the identified grouping of points is a state for the subject in which the subject is unlikely to have an ictal event within the predetermined or computed time period; training the algorithm on the identified grouping of grouping of points; storing the algorithm in a patient monitoring device; and using the algorithm to identify a contra-ictal condition of the subject. In some embodiments, the method includes the step of storing the identified grouping of feature vectors or a mathematical representation of the identified grouping of feature vectors in memory.

Yet another aspect of the invention provides a method of monitoring a subject's neurological condition. In some embodiments, the method includes the steps of analyzing a physiological signal (such as an EEG) from a subject to determine if the subject is in a contra-ictal condition; and if the subject is in a contra-ictal condition, providing an indication (e.g., to the subject and/or to a caregiver) that the subject is in the contra-ictal condition, such as by activating a green light or other visible output. There may be a plurality of outputs, wherein the step of providing the indication involves providing an output that is indicative of one of a plurality of predetermined time periods. An indication can also be the ceasing or absence of an output. Some embodiments include the additional step of providing an input to a closed loop therapeutic system adapted to minimize and/or prevent the occurrence of a seizure.

In some embodiments, if the subject is in a pro-ictal condition, the method includes the step of providing an indication (such as a red light) that the subject is in the pro-ictal condition. Likewise, in some embodiments, if the subject is not in a contra-ictal condition and not in a pro-ictal condition, the method includes the step of providing an indication (such as a yellow light) that the subject is not in either contra-ictal condition or a pro-ictal condition.

In some embodiments, the step of analyzing the physiological signal involves providing at least a portion of the physiological signal as an input to a classifier. The step of analyzing the physiological signal may also include extracting a feature vector from the physiological signal and providing the extracted feature vector as an input to a classifier. In some embodiments, the step of analyzing the physiological signal includes the steps of extracting N features from the physiological signal; generating N dimensional feature vector of the extracted N features for time points of the physiological signal; and determining if the N-dimensional feature vector is within a contra-ictal region in the N-dimensional space.

Still another aspect of the invention provides a subject advisory system having a processing assembly configured and programmed to process a data signal (such as an extracted feature from a physiological signal from the subject) obtained from a subject to determine if the subject is in a contra-ictal condition (e.g., a condition in which the subject is at a low susceptibility to having a seizure within a predetermined time period); and an indication assembly (such as a green light) adapted to provide an indication that the subject is in the contra-ictal condition. Some or all of the processing assembly may be adapted to be implanted within a subject, with any remaining portion of the processing assembly being adapted to be external to the subject. In some embodiments, the indication assembly provides a substantially continuous output that indicates the subject's condition.

Some embodiments of the invention include an implanted communication unit that is in communication with an electrode that samples a physiological signal from the subject, wherein the data signal is indicative of the physiological signal and is substantially continuously transmitted (wirelessly or otherwise) substantially in real-time from the implanted communication unit to the processing assembly.

Yet another aspect of the invention provides a seizure advisory system having an electrode configured to sample an EEG signal from a subject; an implanted communication unit coupled to the electrode, the implanted communication unit configured to transmit a wireless signal from the subject's body; and a subject advisory device that is external to the subject's body. The subject advisory device has a processing assembly that processes the wireless signal to determine if the subject is in a contra-ictal condition; and a user interface that provides an output to the subject that indicates that the subject is in the contra-ictal condition. In some embodiments, the subject advisory device also has a memory for storing the wireless signal.

Still another aspect of the invention provides a method of monitoring a subject's neurological condition. Some embodiments includes the steps of analyzing a physiological signal from the subject; and providing an indication when the subject is highly unlikely to enter an ictal state for a predetermined period of time, providing an indication (such as a green light) when the subject is highly unlikely to have a seizure, providing an indication when the subject is highly unlikely to enter a pro-ictal state, and/or providing an indication when the subject is highly unlikely to have a seizure or to enter a pro-ictal state. In some embodiments the predetermined period of time is greater than 10 minutes, and in some embodiments the predetermined period of time is greater than 90 minutes.

Some embodiments add the step of providing an indication (such as a red light) when the subject has a high susceptibility of entering an ictal state. Some other embodiments also add the step of providing an indication (such as a yellow light) when the subject is not highly unlikely to enter into an ictal state and does not have a high susceptibility of entering an ictal state.

Yet another aspect of the invention provides a method of monitoring a subject's neurological condition. In some embodiments, the method includes the steps of: analyzing a physiological signal from a subject to determine the subject's neurological state; and based on the state determined in the analyzing step, providing an input to a closed loop therapeutic system adapted to alter the neurological state.

Still another aspect of the invention provides a user interface for a seizure advisory system, the user interface having a first indicator (such as a green light) that indicates when the subject is in a contra-ictal condition; a second indicator (such as a red light) that indicates when the subject is in a pro-ictal condition; and a processor that is configured to activate or deactivate the first and second indicator depending on the subject's estimated condition. The first and second indicators may be discrete indicators on the user interface. The user interface may also have a third indicator (such as a yellow light) that indicates when the subject is not in the contra-ictal condition or the pro-ictal condition.

Yet another aspect of the invention provides a user interface for a seizure advisory system, the user interface having: an indicator that indicates when the subject is in a contra-ictal condition and a pro-ictal condition; and a processor that is configured to activate or deactivate the indicator based on the subject's estimated condition.

Another aspect of the invention provides a user interface for a seizure advisory system, with the user interface having a first indicator that indicates when the subject is unlikely to transition to a pro-ictal condition within a period of time; a second indicator that indicates when the subject is in a pro-ictal condition; and a processor that is configured to activate or deactivate the first and second indicator depending on the subject's estimated condition. In some embodiments, the first indicator also indicates when the subject is unlikely to transition to an ictal condition within a period of time.

Still another aspect of the invention provides a user interface for a seizure advisory system, the user interface having a first indicator that indicates when the subject is unlikely to transition to an ictal condition within a period of time; a second indicator that indicates when the subject is in a pro-ictal condition; and a processor that is configured to activate or deactivate the first and second indicator depending on the subject's estimated condition.

The term "state" is used herein to generally refer to calculation results or indices that are reflective of the state of the subject's neural system, but does not necessarily constitute a complete or comprehensive accounting of the subject's total neurological condition. The estimation and characterization of "state" may be based on one or more subject dependent parameters from the brain, such as electrical signals from the brain, including but not limited to electroencephalogram signals "EEG" and electrocorticogram signals "ECoG" (referred to herein collectively as "EEG"), brain temperature, blood flow in the brain, concentration of AEDs in the brain, or other physiological signals). The term "pro-ictal" is used herein to refer to a neurological state or condition characterized by a high susceptibility of transition to an ictal state. A pro-ictal state may transition to either an ictal or inter-ictal state.

For a further understanding of the nature and advantages of the present invention, reference should be made to the following description taken in conjunction with the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 15 illustrates one embodiment of an external data device.

DETAILED DESCRIPTION OF THE INVENTION

Figure 1A:
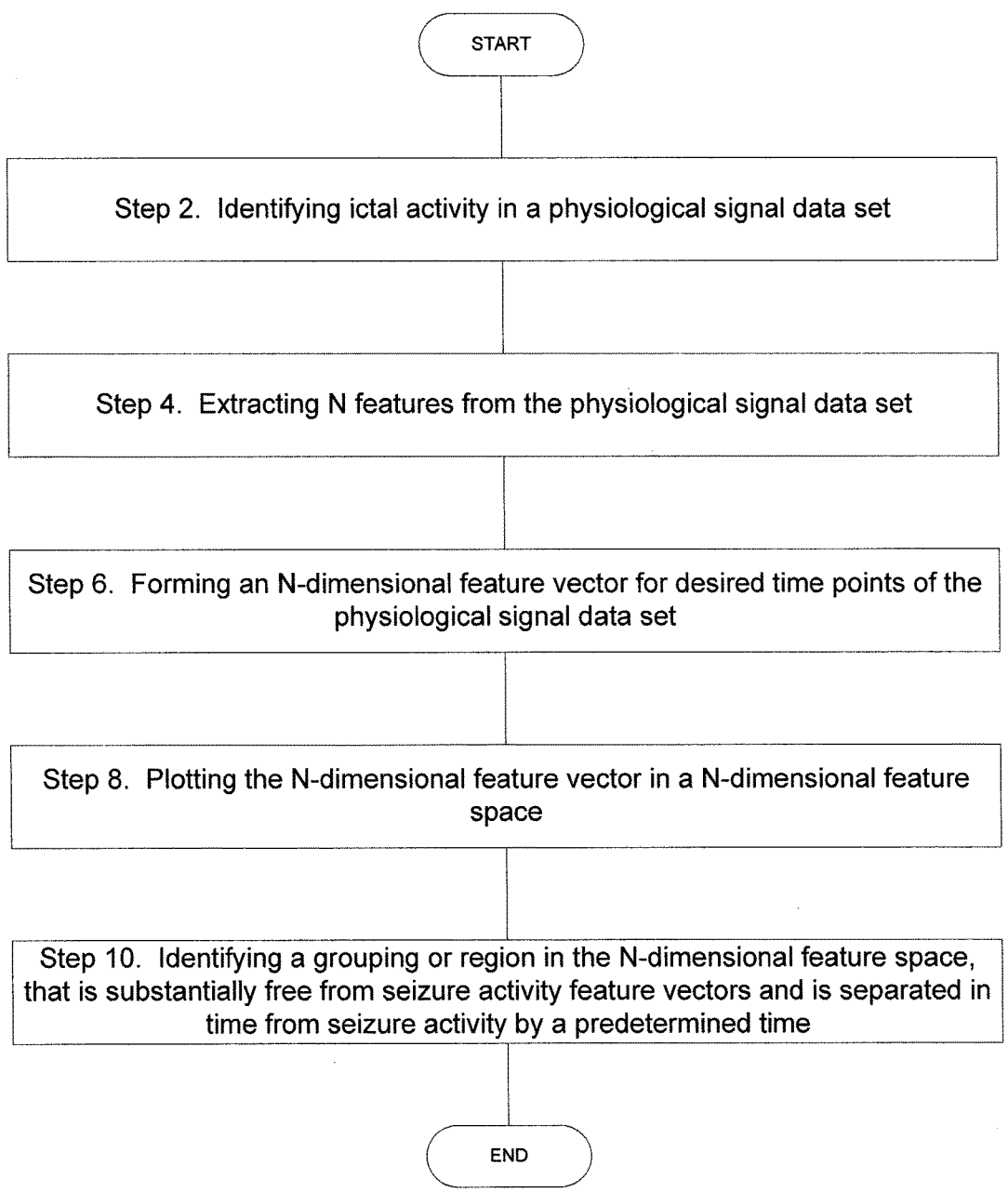
FIG. 1A is a simplified method of identifying a contra-ictal condition in a subject data set according to one embodiment of the invention.

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

While the discussion below focuses on measuring electrical signals generated by electrodes placed near, on, or within the brain or nervous system (EEG signals) of subjects and subject populations for the determination of when an epileptic subject is in a contra-ictal condition, it should be appreciated that the invention is not limited to measuring EEG signals or to determining when the subject is in a contra-ictal state. For example, the invention could also be used in systems that measure one or more of a blood pressure, blood oxygenation (e.g., via pulse oximetry), temperature of the brain or of portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

Furthermore, while the remaining discussion focuses on identifying a contra-ictal condition for epileptic subjects, the present invention may also be applicable to monitoring other neurological or psychiatric disorders and identifying a condition or state for such disorders in which the subject is unlikely to experience some adverse effect. For example, the present invention may also be applicable to monitoring and management of sleep apnea, Parkinson's disease, essential tremor, Alzheimer's disease, migraine headaches, depression, eating disorders, cardiac arrhythmias, bipolar spectrum disorders, or the like. As can be appreciated, the features extracted from the signals and used by the algorithms will be specific to the underlying disorder that is being managed. While certain features may be relevant to epilepsy, such features may or may not be relevant to the state measurement for other disorders.

One embodiment of the present invention identifies and uses a contra-ictal classification for each subject in which the subject is highly unlikely to transition to the ictal state within a specified time period. The contra-ictal condition can be considered to be a subset of the inter-ictal class or it can be considered to be a completely new neurological classification. While it is beneficial to the subject to know if the subject is in the inter-ictal condition, being in the inter-ictal condition does not necessarily inform the subject that they will not quickly transition from the inter-ictal condition to the ictal condition. Being able to inform a subject that they are in a contra-ictal state can allow the subject to engage in normal daily activities, such as driving a car, or walking down a set up stairs, without fearing that they will have a seizure or without fearing that they may quickly transition into a pro-ictal state. Knowing when a seizure is unlikely to occur can be even more important to the subject's freedom than being alerted when a seizure it likely to occur.

The period of time associated with the contra-ictal state will vary depending on the implementation of the algorithm. The period of time could be a predetermined time period as determined from the training data and programmed into the algorithm, such as 10 minutes, 20 minutes, 30 minutes, 60 minutes, 90 minutes or more. In other implementations, the algorithm could compute the period, which may be different from episode to episode for a single subject. Thus, for some subjects, the period of time could span many hours or even days or weeks.

One aspect of the present invention provides systems and methods for identifying a contra-ictal state or condition of the subject. Most conventional seizure prediction systems only attempt to differentiate between a pre-ictal state and an inter-ictal state for purposes of seizure prediction. Advantageously, the present invention further identifies the contra-ictal condition or state for the particular patient.

Figure 9:
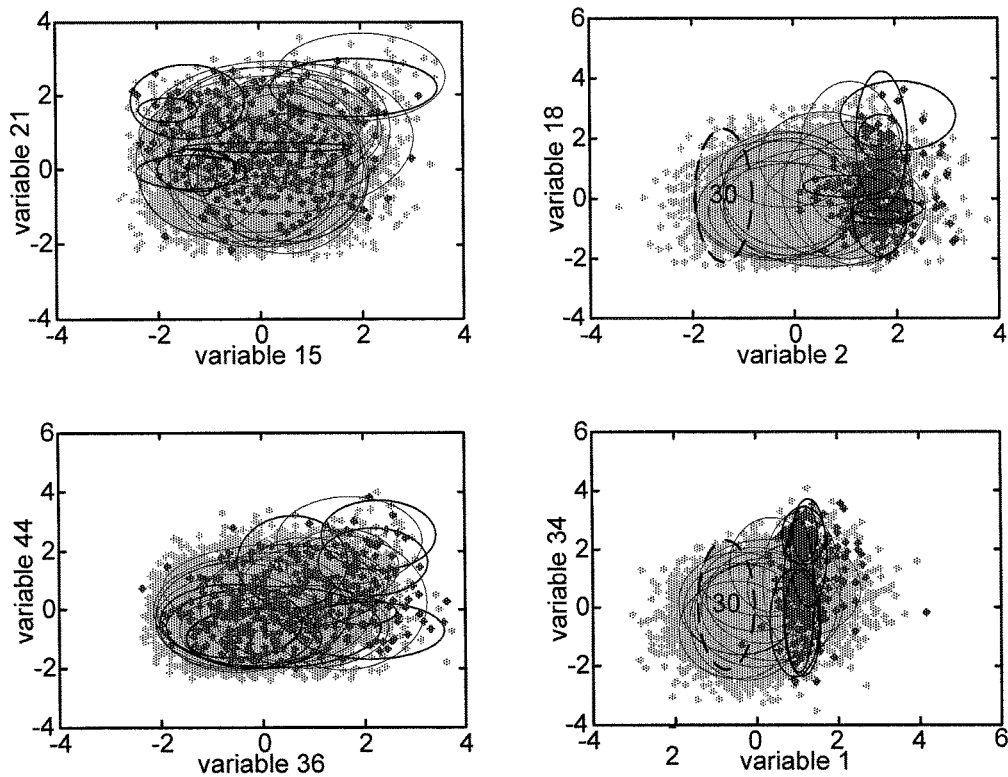
FIG. 9 illustrates a plotting of two-dimensional feature vectors in a two-dimensional feature space with different combination of variables (features).

FIG. 1A illustrates a simplified method of identifying a contra-ictal state for the subject. The method of FIG. 1A is typically performed in a computer system in a physician's office, but it could also be performed in a central processing computer workstation remote from the physician, or even in a patient's external data device or implanted communication unit (FIG. 9).

At step 2, a training dataset of the subject is obtained and annotated to identify the ictal activity. The training data could span days or weeks, and is preferably a substantially continuous monitoring of the patient's EEG signals using an array of intracranial electrodes. Preferably the training data comprises a plurality of ictal events separated by inter-ictal intervals. For epilepsy, the training set of physiological signals typically includes a training set of intracranial EEG recordings from subject's long term visit to an epilepsy monitoring unit (EMU). However, the EEG training sets could be obtained from the ambulatory system described below in relation to FIGS. 9 to 11.

While EEG signals are currently the desirable physiological signals that are analyzed, any of the aforementioned physiological signals could be used to train the algorithms. As is known in the art, the training set may be overlaid with comments from a physician and/or a marking algorithm may automatically identify some or all of the ictal activity in the training set—such as epileptiform spikes, earliest electrographic change (EEC), unequivocal electrical onset of seizure (UEO), unequivocal clinical onset (UCO), end of electrographic seizure (EES), etc. The following Steps 4-10 which are described in the subsequent paragraphs are directed towards EEG signals, however, such analysis may also be applied to the aforementioned other physiological signals.

Figure 6:
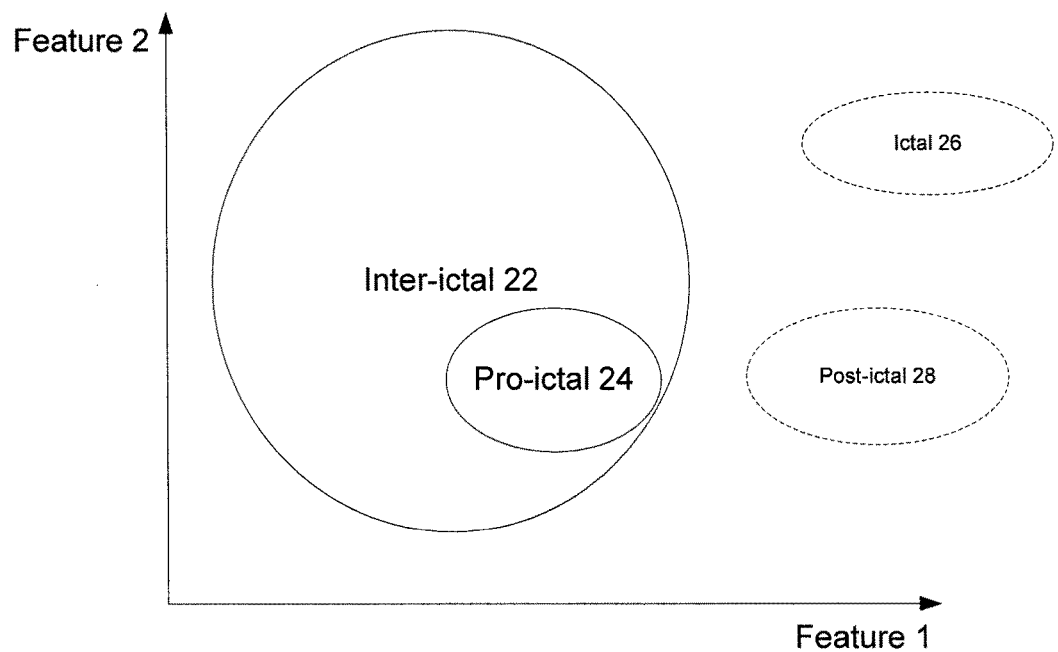
FIG. 6 illustrates one example of a classification method in 2D feature space.
Figure 7:
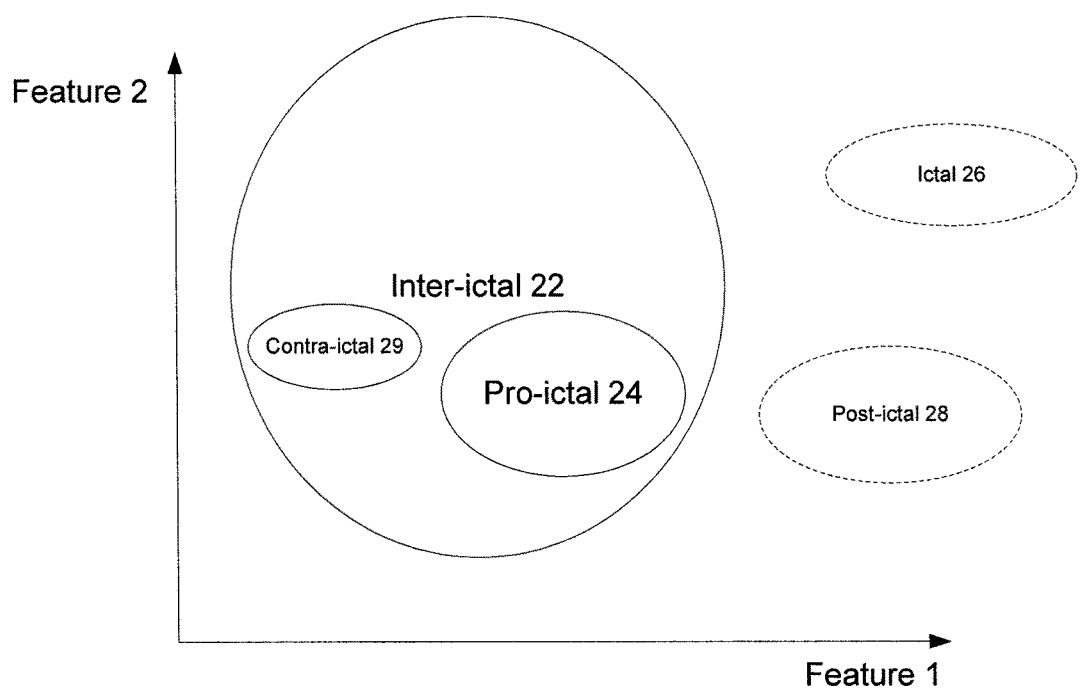
FIGS. 7 and 8 illustrate various classification methods encompassed by the present invention which include a contra-ictal class in 2D feature space.
Figure 8:
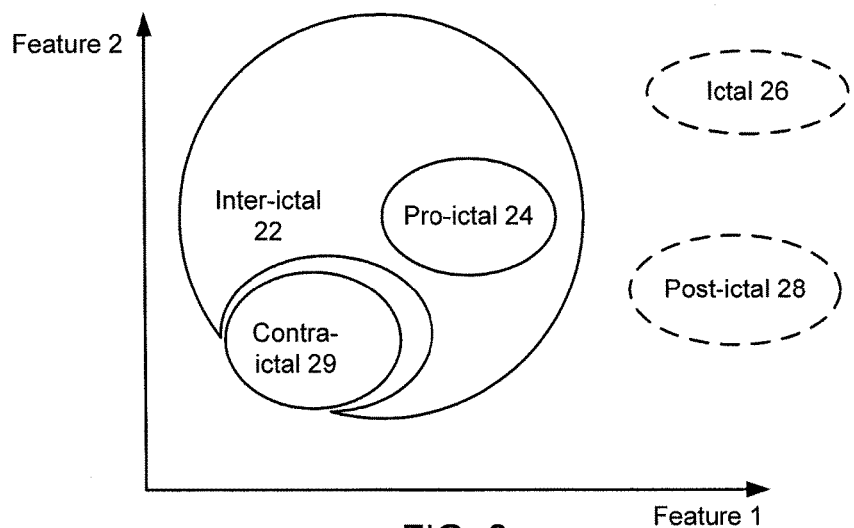

At step 4, N feature extractors may be applied to the training set to quantify relevant aspects of the EEG training dataset. Any number of features can be extracted from the EEG signals in order to assess the subject's condition. At step 6, for each desired point in time in the EEG training dataset, an N-dimensional feature vector will be formed for each of the N features that are extracted. At step 8, if desired, the extracted N-dimensional feature vectors may then be allocated or plotted in an N-dimensional feature space. While not shown in FIG. 1A, the invention may also be used with lower dimension spaces created through application of data transformations to the N-dimensional feature vector, including but not limited to, principle components analysis, factor analysis, or linear discriminant analysis. For ease of reference, FIGS. 6 to 8 illustrate a plot of feature vectors across a two dimensional space (N=2), but it should be appreciated that any dimensional space could be used with the present invention.

Since it is not likely for the physician or training system to identify a contra-ictal period a priori, one aspect of the present invention utilizes an unsupervised learning protocol to identify a contra-ictal condition for the subject by utilizing an algorithm or other means to identify a region of the feature space or clusters or groupings of feature vectors in the N-dimensional feature space that are substantially devoid of feature vectors that are in an ictal condition and for which all feature vectors in the grouping or region are separated from an ictal event (e.g., seizure) by a predetermined time period (step 10). For example, the N-dimensional feature space may be partitioned into a collection of N-dimensional hypercubes. A hypercube that is substantially devoid of training vectors that occur within a predetermined time period prior to the next seizure may be labeled contra-ictal. In another implementation, a binary space partitioning algorithm can be used to partition the N-dimensional feature space into a collection of N-dimensional hyperprisms. A hyperprism that is substantially devoid of training vectors that occur within a predetermined time period prior to the next seizure may be labeled contra-ictal. In another implementation, the structure of the training data may be approximated by an expansion of radial basis function, e.g. a Gaussian mixture model. Each feature vector in the training data may be assigned to one component of the radial basis function expansion using, e.g., Bayesian posterior probability or decision risk criteria. A component that is substantially devoid of training vectors that occur within a predetermined time period prior to the next seizure may be labeled contra-ictal. The algorithm may also identify other classes of interest from the EEG training dataset (e.g., inter-ictal that is not part of the contra-ictal class, pro-ictal, ictal, post-ictal, or the like), and the classes of interest (or groupings of feature vectors) for the patient and/or mathematical representations thereof are stored in memory for later use in the subject system implanted or otherwise used by the subject.

It is further noted that each identified partition in the N-dimensional feature space can be assigned an identifier that may be used to represent states in a Markov chain, or symbols emitted by hidden states in a hidden Markov model. These identifiers, or sequences of identifiers may be used to make inferences about future states, and thereby the likelihood of seizure occurrence.

Similar approaches may be used to derive and train a pro-ictal algorithm. For example, an algorithm or other means may be used to identify a region of the feature space or clusters or groupings of feature vectors in the N-dimensional feature space that frequently precede an ictal state by a predetermined period of time but occur infrequently in inter-ictal intervals. Alternatively, a prior art seizure prediction algorithm may be used.

Figure 1B:
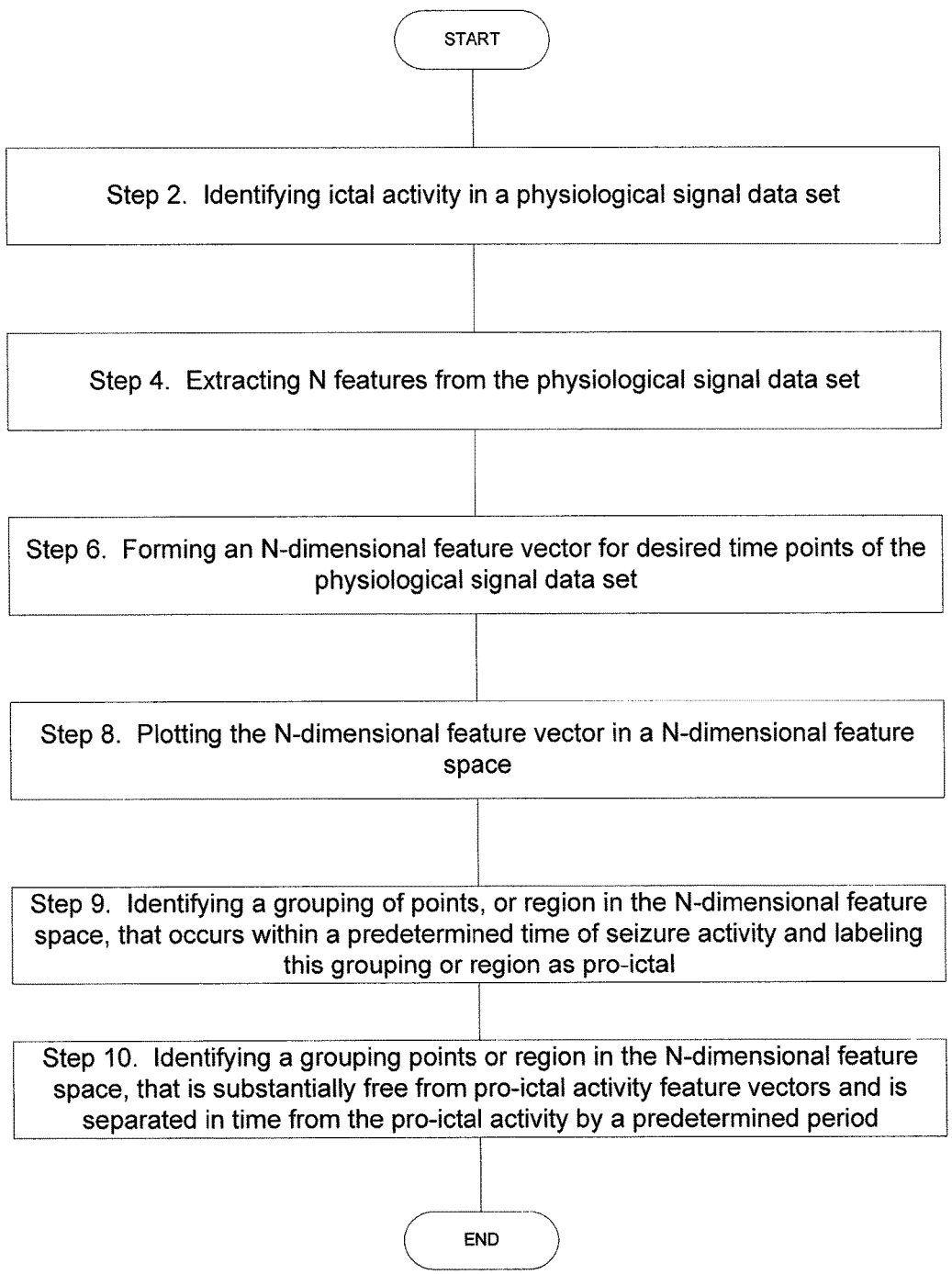
FIG. 1B is a simplified method of identifying a contra-ictal condition in a subject data set according to another embodiment of the invention.

FIG. 1B shows another embodiment of a method of identifying a contra-ictal state for a subject. This method tracks the method of FIG. 1A for steps 2, 4, 6 and 8. FIG. 1B adds a step 9, however, that involves identifying a grouping of points or a region in the N-dimensional feature space that occurs within a predetermined time of seizure activity. This group or region is labeled "pro-ictal." In step 10 of this method, the method then identifies a grouping of points or a region in the N-dimensional feature space that is substantially free from pro-ictal activity feature vectors and is separated in time from the pro-ictal activity by a predetermined time period using, e.g., the techniques discussed above with respect to step 10 of FIG. 1A.

Figure 1C:
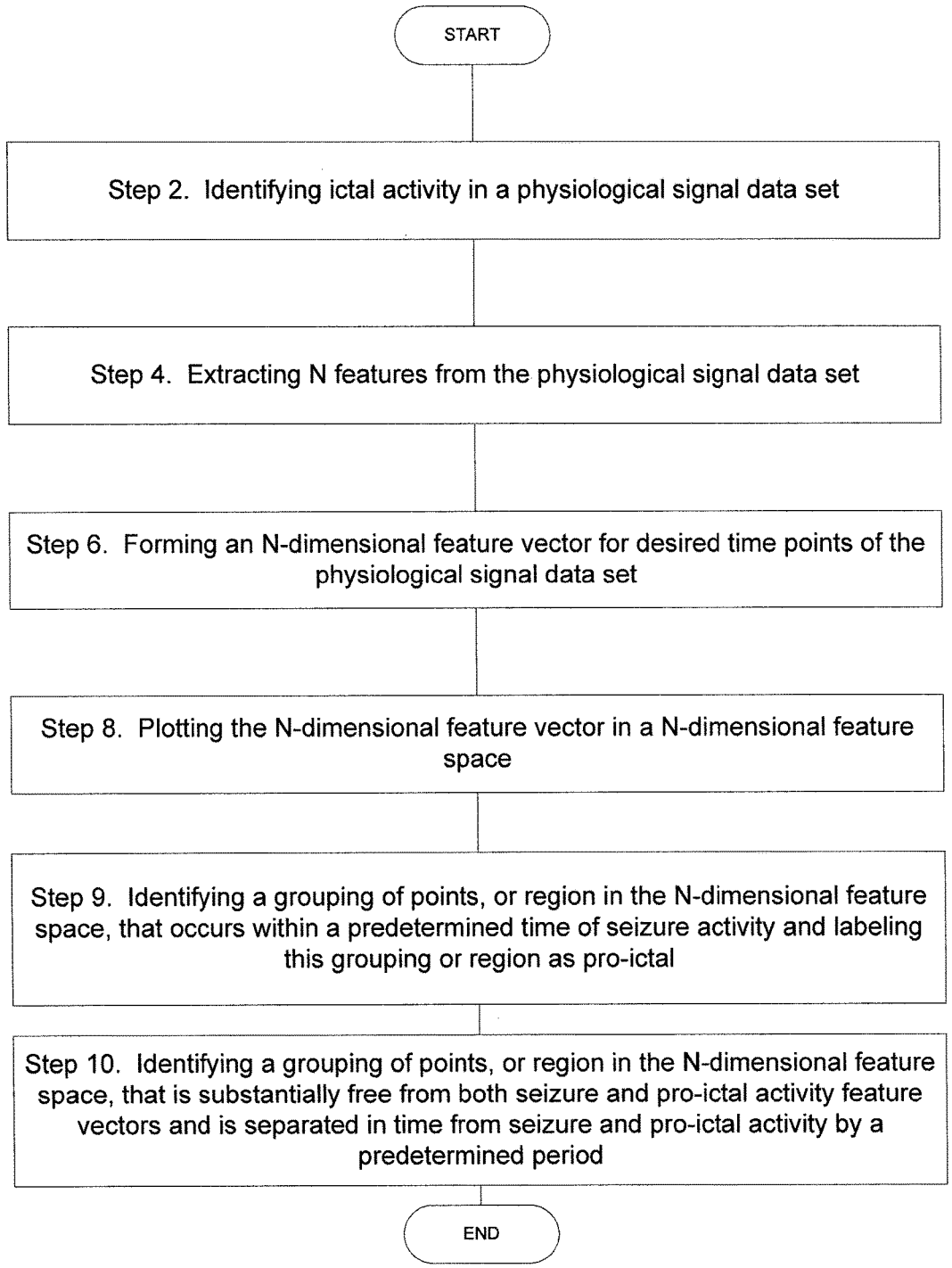
FIG. 1C is a simplified method of identifying a contra-ictal condition in a subject data set according to yet another embodiment of the invention.

FIG. 1C shows yet another embodiment of a method of identifying a contra-ictal state for a subject. Once again, this method tracks the method of FIG. 1A for steps 2, 4, 6 and 8. Like the method of FIG. 1B, FIG. 1C adds a step 9 that involves identifying a grouping of points or a region in the N-dimensional feature space that occurs within a predetermined time of seizure activity. This group or region is labeled "pro-ictal." In step 10 of this method, the method then identifies a grouping of points or a region in the N-dimensional feature space that is substantially free from both pro-ictal activity feature vectors and seizure feature vectors, and is separated in time from the seizure and pro-ictal activity by a predetermined time period using, e.g., the techniques discussed above with respect to step 10 of FIG. 1A.

Figure 2:
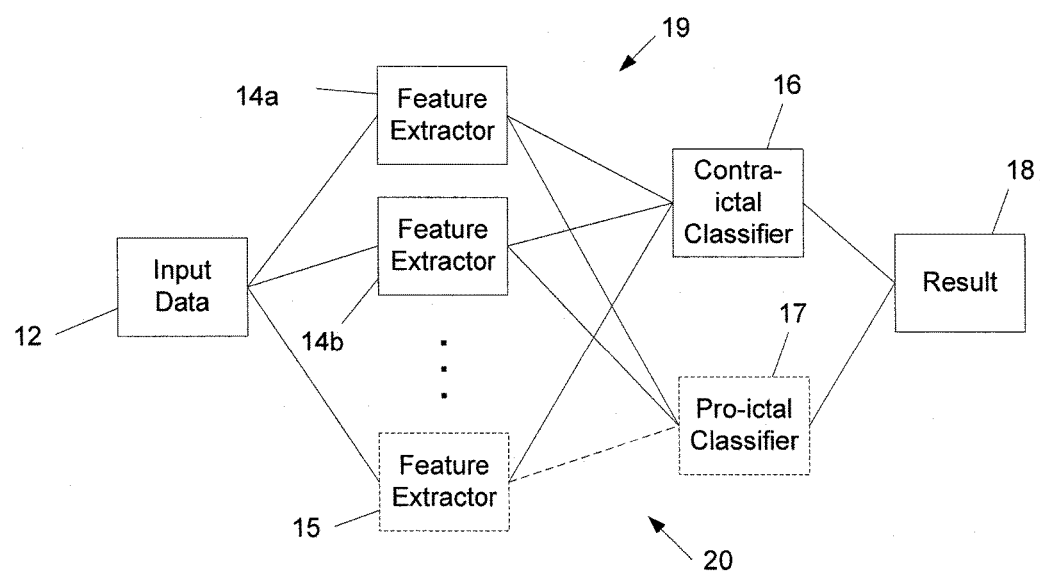
FIG. 2 schematically illustrates a plurality of algorithms that may be embodied by the present invention.

Once the algorithm has been trained to identify the different classes for the subject, the algorithm may be embodied or otherwise uploaded into a subject system for performing substantially real-time monitoring and assessment of the subject's brain activity. FIG. 2 depicts an example of the overall structure of a system for performing substantially real-time assessment of the subject's brain activity and for determining the communication output that is provided to the subject. The system may comprise one or more algorithms or modules that process input data 12. The algorithms may take a variety of different forms, but typically comprises one or more feature extractors 14a, 14b, 15 and at least one classifier 16, 17. The embodiment illustrated in FIG. 2 shows a contra-ictal algorithm 19 and a pro-ictal algorithm 20 which share at least some of the same feature extractors 14a, 14b. In alternative embodiments, however, the algorithms used in the system may use exactly the same feature extractors or completely different feature extractors (not shown).

The input data 12 is typically EEG, but may comprise representations of physiological signals obtained from monitoring a subject and may comprise any one or combination of the aforementioned physiological signals from the subject. The input data may be in the form of analog signal data or digital signal data that has been converted by way of an analog to digital converter (not shown). The signals may also be amplified, preprocessed, and/or conditioned to filter out spurious signals or noise. For purposes of simplicity the input data of all of the preceding forms is referred to herein as input data 12. In one preferred embodiment, the input data comprises between about 1 channel and about 64 channels of EEG from the subject.

The input data 12 from the selected physiological signals is supplied to the one or more feature extractors 14a, 14b, 15. Feature extractor 14a, 14b, 15 may be, for example, a set of computer executable instructions stored on a computer readable medium, or a corresponding instantiated object or process that executes on a computing device. Certain feature extractors may also be implemented as programmable logic or as circuitry. In general, feature extractors 14a, 14b, 15 can process data 12 and identify some characteristic of interest in the data 12. Feature extractors used in the subject system are typically the same feature extractors used in the method described in the method of FIG. 1. Such a characteristic of the data is referred to herein as an extracted feature.

Each feature extractor 14a, 14b, 15 may be univariate (operating on a single input data channel), bivariate (operating on two data channels), or multivariate (operating on multiple data channels). Some examples of potentially useful characteristics to extract from signals for use in determining the subject's propensity for a neurological event, include but are not limited to, bandwidth limited power (alpha band [8-13 Hz], beta band [13-18 Hz], delta band [0.1-4 Hz], theta band [4-8 Hz], low beta band [12-15 Hz], mid-beta band [15-18 Hz], high beta band [18-30 Hz], gamma band [30-48 Hz], high frequency power [>48 Hz], bands with octave or half-octave spacings, wavelets, etc.), second, third and fourth (and higher) statistical moments of the EEG amplitudes or other features, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STL-max, T-index, angular frequency, and entropy), line length calculations, first, second and higher derivatives of amplitude or other features, integrals, and mathematical linear and non-linear operations including but not limited to addition, subtraction, division, multiplication and logarithmic operations. Of course, for other neurological conditions, additional or alternative characteristic extractors may be used with the systems described herein.

The extracted characteristics can be supplied to the one or more classifiers 16, 17. Like the feature extractors 14a, 14b, 15, each classifier 16, 17 may be, for example, a set of computer executable instructions stored on a computer readable medium or a corresponding instantiated object or process that executes on a computing device. Certain classifiers may also be implemented as programmable logic or as circuitry.

The classifiers 16, 17 analyze one or more of the extracted characteristics, and either alone or in combination with each other (and possibly other subject dependent parameters), provide a result 18 that may characterize, for example, a subject's condition. The output from the classifiers may then be used to determine the output communication that is provided to the subject regarding their condition. As described above, the classifiers 16, 17 are trained by exposing them to training measurement vectors, typically using supervised methods for known classes, e.g. ictal, and unsupervised methods as described above for classes that can't be identified a priori, e.g. contra-ictal. Some examples of classifiers include k-nearest neighbor ("KNN"), binary and higher order space partitions, linear or non-linear regression, Bayesian, mixture models based on Gaussians or other basis functions, neural networks, and support vector machines ("SVM"). Each classifier 16, 17 may provide a variety of output results, such as a logical result or a weighted result. The classifiers 16, 17 may be customized for the individual subject and may be adapted to use only a subset of the characteristics that are most useful for the specific subject. Additionally, over time, the classifiers 16, 17 may be further adapted to the subject, based, for example, in part on the result of previous analyses and may reselect extracted characteristics that are used for the specific subject.

For the embodiment of FIG. 2, the pro-ictal classifier 17 may classify the outputs from feature extractors 14a, 14b to detect characteristics that indicate that the subject is at an elevated susceptibility for a neurological event, while the contra-ictal classifier 16 may classify the outputs from feature extractors 14a, 14b, 15 to detect characteristics that occur when the subject is unlikely to transition into an ictal condition for a specified period of time. The combined output of the classifiers 16, 17 may be used to determine the output communication provided to the subject. In embodiments which comprise only the contra-ictal algorithm, the output from the contra-ictal classifier 16 alone may be used to determine the output communication to the subject.

Figure 3:
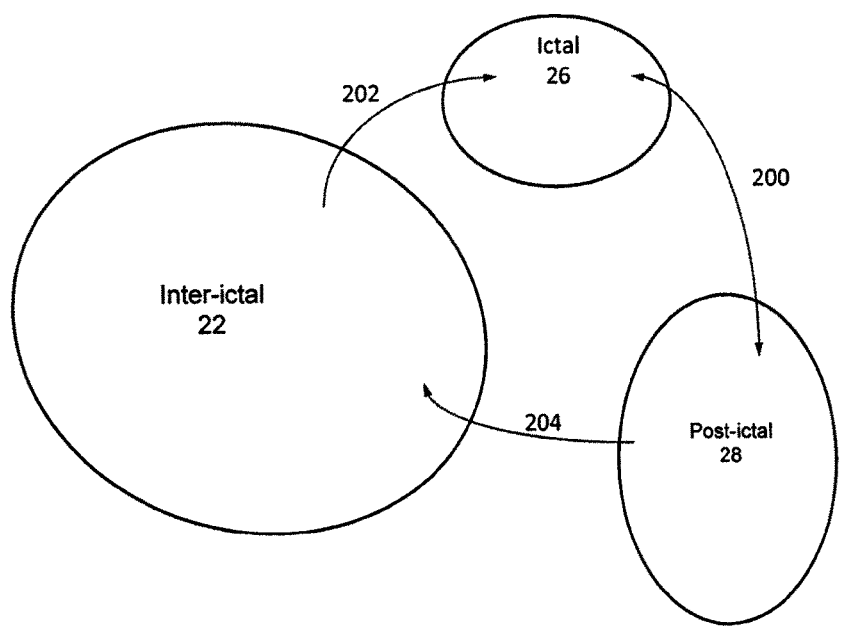
FIG. 3 is a diagram illustrating three neurological states of epilepsy (ictal, post-ictal and interictal).

FIG. 3 illustrates a Venn diagram illustrating a simplified approximation of the relationship of the neurological states or conditions of patients diagnosed with epilepsy. The ictal state 26 is the actual period in which the subject is experiencing a seizure. As previously mentioned, the "average" subject is in the ictal state approximately 0.02% of the overall time. Therefore, the associated sizes of the Venn diagram set areas are not meant to be representative of the overall time the subject is in the various states, otherwise, the ictal period would be approximately 5,000 times smaller than the interictal period. The interictal state 22 is sometimes termed the "normal" neurological state and represents the neurological state between seizures. The post-ictal state 28 is the neurological state immediately following a seizure or ictal 26 state. Also depicted in this three state model are the transitions. During the onset of a seizure the neurological state transitions 202 from the interictal state to the ictal state. Upon termination of the seizure the neurological state transitions 200 to the post-ictal state and then transitions 204 to the interictal state. During seizure clustering it is also possible for the patient to transition 200 from the post-ictal state to the ictal state.

Figure 4:
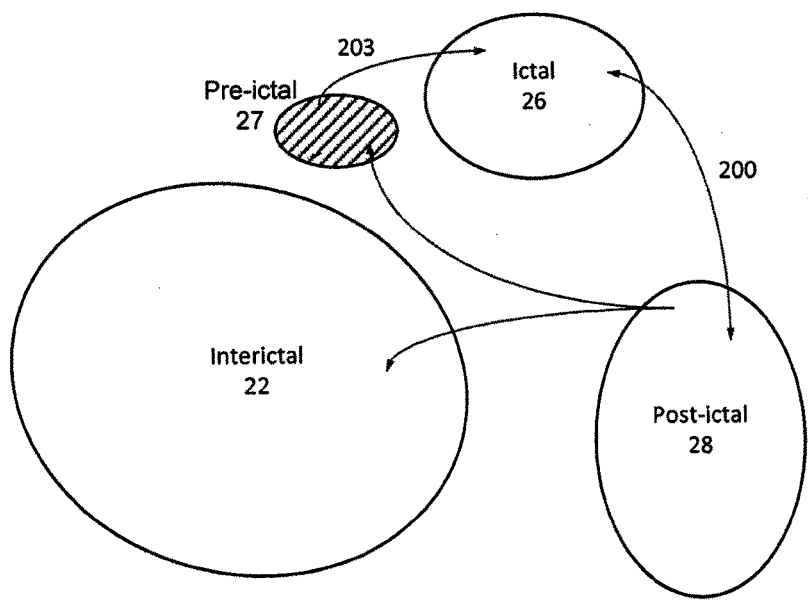
FIG. 4 is a diagram illustrating the three neurological states as well as a pre-ictal period.

FIG. 4 illustrates an additional state, pre-ictal 27, which occurs between the interictal state and the seizure or ictal state. Some researchers have proposed that seizures develop minutes to hours before the clinical onset of the seizure. These researchers therefore classify the "pre-ictal" condition as the beginning of the ictal or seizure event which begins with a cascade of events. Under this definition, a seizure is imminent and will occur (e.g. transition 203 from pre-ictal to ictal) if a pre-ictal condition is observed. There have been a number of proposals from groups around the world for predicting seizures and warning the subject of the impending seizure. Most of such proposals attempt to analyze the subject's electroencephalogram or electrocorticograms (referred to collectively as "EEGs"), to differentiate between a "pre-ictal condition" (i.e., pre-seizure condition) and an "interictal condition" (i.e., between seizures). To date, however, none of the proposed systems have proven to be effective in predicting seizures. With this additional state in the state diagram of FIG. 4, we see that it is possible to transition from the post-ictal state either to pre-ictal, interictal or ictal.

Figure 5:
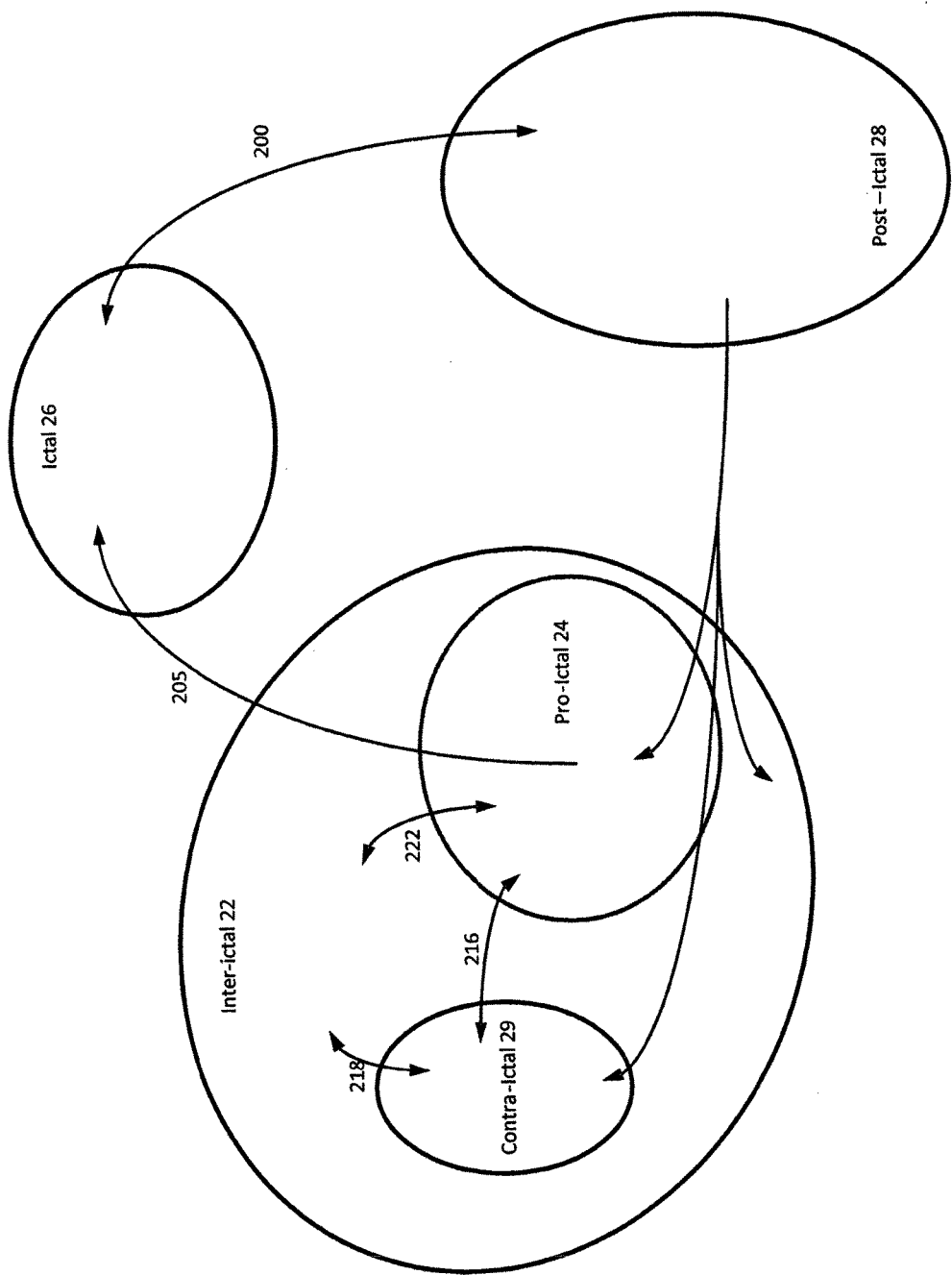
FIG. 5 is a diagram illustrating the three neurological states as well as contra-ictal and pro-ictal states.

FIG. 5 illustrates two additional neurological states. These states, contra-ictal and pro-ictal, are shown as subsets within the Interictal state. The contra-ictal state 29 is referred to as a "low susceptibility to seizure" condition for a time period. The pro-ictal state 24 represents a neurological state having a high susceptibility for a seizure. As shown it is possible for the neurological contra-ictal state to transition back into the general interictal state (transition 218) or into a pro-ictal state (transition 216). As shown by transitions 216, 222 and 205, it is possible for the neurological pro-ictal state to transition to the contra-ictal state, the interictal state or the ictal state. The subject may also go from an interictal state to an ictal state.

FIGS. 6 to 12 illustrate different aspects of the systems encompassed by the present invention. The classifiers may have multiple classes (e.g., two or more), may provide a weighted answer, or they may provide an output that is expressed as a continuum between the contra-ictal and pro-ictal conditions, with a scalar or vector of parameters describing the actual condition and its variations. For example, as shown in FIG. 6, a multiple class classifier may have labels such as 'inter-ictal' 22, 'pro-ictal' 24, 'ictal' 26, or 'post-ictal' 28. In other embodiments shown in FIG. 11, the classifiers 16, 17 are one-class classifiers that calculate probability of class membership (probability of pro-ictal, probability of contra-ictal).

Referring now to FIGS. 7 and 8, as it relates to the seizure advisory system of the present invention, one implementation of a classification of conditions defined by the classifiers 16, 17 include (1) an inter-ictal class 22 (sometimes referred to as a "normal" condition), (2) a pro-ictal class 24 (sometimes referred to as an "abnormal" or "high-susceptibility to seizure" condition), (3) an ictal class 26 (sometimes referred to as a "seizure" condition), (4) a post-ictal class 28 (sometimes referred to as a "post-seizure" condition), and (5) a contra-ictal condition 29 (sometimes referred to as a "low susceptibility to seizure for a time period" condition). FIG. 7 illustrates the contra-ictal class 29 as a sub-set of the inter-ictal class 28 while FIG. 8 illustrates the contra-ictal class 29 as a separate class from the inter-ictal class 28.

FIG. 9 illustrates an example of 2-dimensional projections of an N-dimensional feature space extracted from patient physiological data, such as EEG data. The dark data points are feature vectors that occur within 20 minutes of a subsequent seizure. These data points are therefore labeled pro-ictal. The lighter points are inter-ictal feature vectors that occur more than 3 hours prior to a seizure. As shown in the projection onto variables 15 and 21 and variables 36 and 44 in the left column of FIG. 9, there does not appear to be any differentiable clusters or groupings between the two groups. However, for the projection onto variable 2 and 18 and variable 1 and 34 in the right column of FIG. 9, there is a more defined separation between the two classes. While the pro-ictal class is included in the interictal class, there are areas outlined by the dotted lines 30 in both two-dimensional projections that are substantially free of pro-ictal feature vectors.

Figure 10:
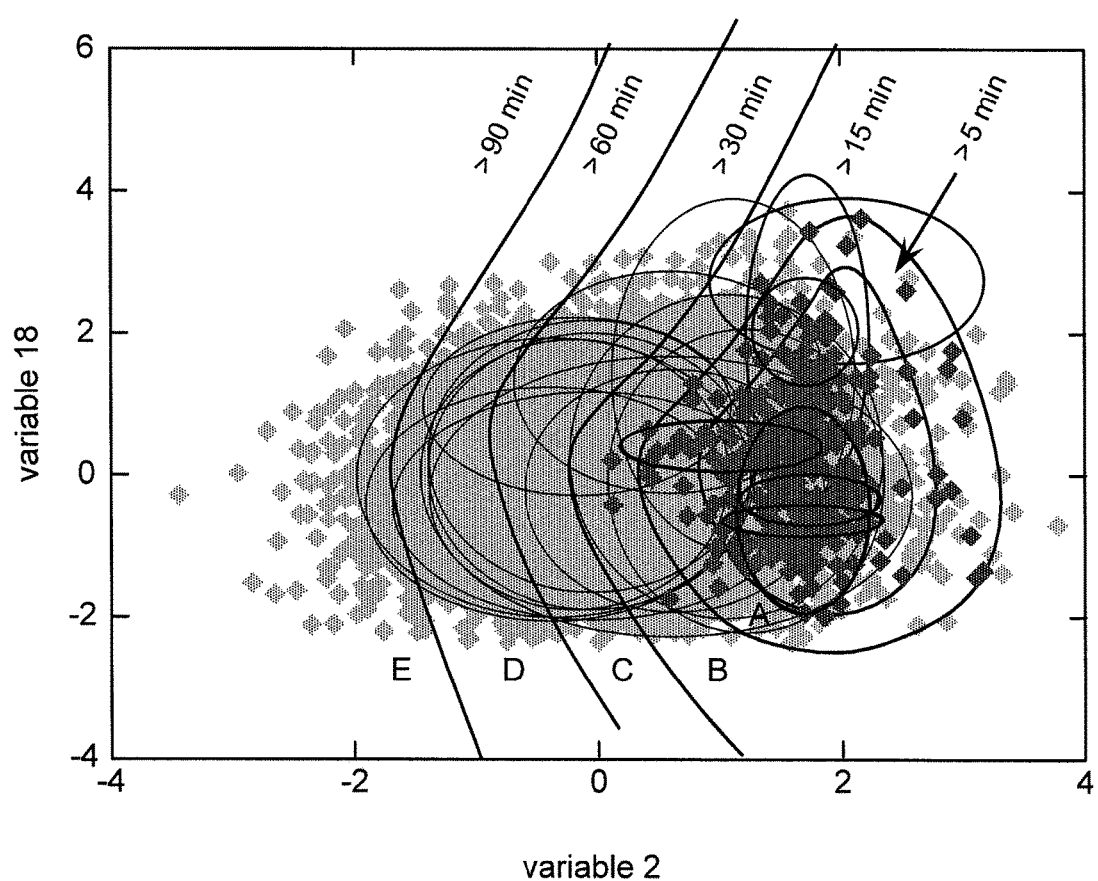
FIG. 10 illustrates a plotting of two-dimensional feature vectors in a two dimensional feature space with contours indicating minimum time to seizure.

The feature classification approach of FIG. 9 can be adapted to develop contra-ictal state detection algorithms for predetermined time periods of other lengths during which a seizure is unlikely. FIG. 10 illustrates one of the 2-dimensional projections of an N-dimensional features space of FIG. 9 for variable 2 versus 18. Added to this 2D projection are contour lines regarding the time elapsed prior to a seizure. For the area marked by "A" all the feature vectors occur more than 5 minutes prior to a seizure. For the area marked by "B" all the feature vectors occur more than 15 minutes prior to the seizure. For areas marked by "C", "D", "E" all of the feature vectors occur more than 30, 60 and 90 minutes prior to the seizure, respectively. Using this 2-dimensional projection one may also adjust/customize the green light for indicating the "contra-ictal" state by selecting the time to seizure contour line (e.g. 15, 30, 60, 90, etc.).

Figures 11, 12:
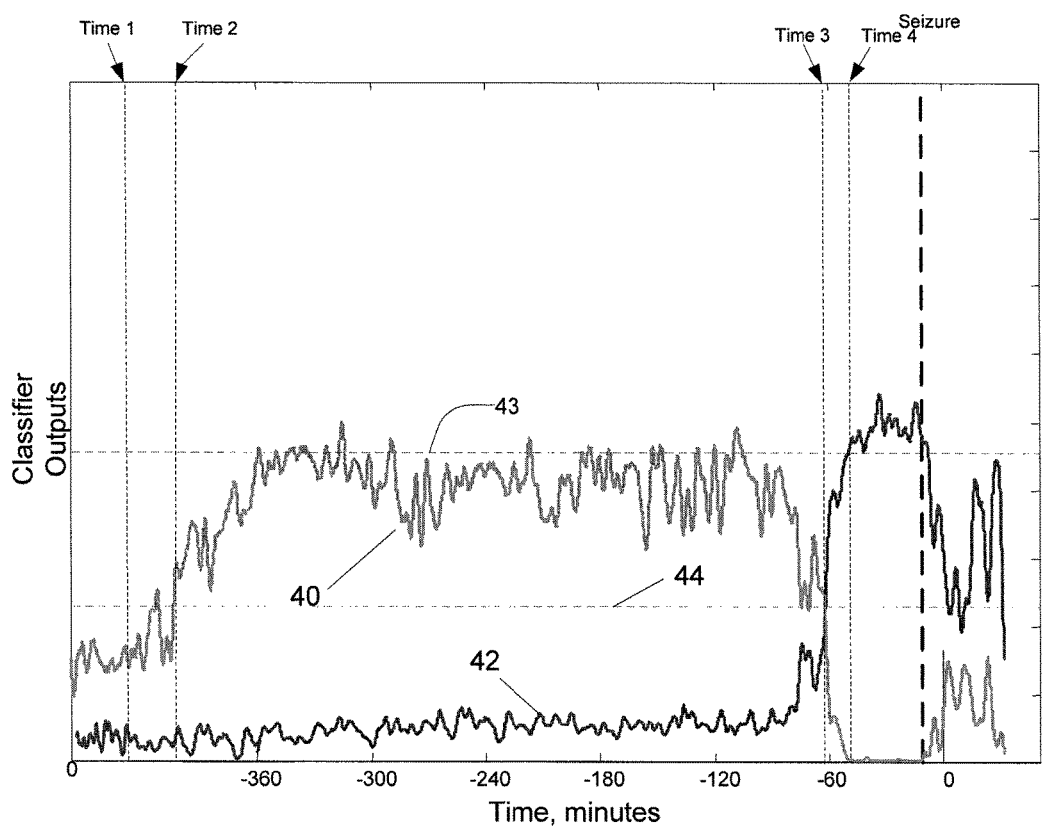
FIG. 11 is an overlay of an output from a contra-ictal classifier over an output of a pro-ictal classifier.
FIG. 12 is a sample truth chart that may be used to determine a communication output provided to the subject.

After deriving the feature vectors that may be used to classify patient physiological signals as being contra-ictal, pro-ictal, etc., these feature vectors may be used to train or form an algorithm for use in a patient monitoring device. FIGS. 11 and 12 illustrate how the outputs from two one-state classifiers within a trained analysis algorithm in a patient monitoring device may be used to determine the output communication provided to the subject. FIG. 11 illustrates an example of the output from the contra-ictal classifier 40 overlaid on an output from the pro-ictal classifier 42. Unlike prior art seizure monitoring devices that looked only for features corresponding to ictal or pre-ictal activity, these classifiers classify extracted features against earlier-derived features to determine whether the extracted features correspond to pro-ictal activity and whether the extracted features correspond to contra-ictal activity. The right-most dotted line indicates where the seizure started. FIG. 12 is a truth table 50 that processes the outputs from the classifiers to determine the output communication provided to the subject.

The truth table 50 of FIG. 12 shows the different possible combinations of outputs from the each of the classifiers and the associated output communication provided to the subject. In one simplified embodiment, the potential output to the subject includes a green light, a yellow light and a red light. A green light may indicate to the subject that they are at a low susceptibility to a seizure for a time period. A yellow light (or some other indication) may indicate to the subject to proceed with caution. Such an indication does not necessarily mean that the subject is at a high susceptibility to have a seizure, but it does mean that it is possible to have a seizure within a predetermined time (such as 90 minutes, etc.). Finally, a red light (or some other indication) may indicate to the subject that they are at an elevated susceptibility for a seizure.

It should be appreciated however, that while FIGS. 11 and 12 describe providing an output to the subject in the form of yellow lights, green lights and red lights, the present invention embodies any number of different type of outputs may be provided to the subject to indicate their condition. The subject's condition could, alternatively, be indicated by the absence of an output. For example, the system could comprise a yellow light and a red light, and the lack of either the red light or yellow light being illuminated would indicate the subject is in a contra-ictal state. The outputs may be different displays on a screen to the patient, different tactile outputs (e.g., vibrations), different sounds, different lights, or any combination thereof. Additionally, such outputs are not limited to the patient/subject, rather the output may be provided to a caregiver. Caregivers may include a physician, nurse or relative, or the like. Furthermore, such output may also provide the inputs to either a closed loop or open loop therapeutic response which attempts to minimize and/or prevent a seizure occurrence. Such therapeutic approaches may include, without limitation, vagus nerve stimulation, deep brain stimulation, neurostimulation, automated/semi-automated or manual dispensing of antiepileptic drugs, and biofeedback techniques.

Referring again to FIG. 11, at Time 1, both classifier outputs 40, 42 are considered to below an artificially specified threshold 44 and are both considered to be "low." In this embodiment, anything below the threshold 44 indicates that there is a low likelihood that the subject is in a pro-ictal state and/or a low likelihood that the subject is in a contra-ictal state. Since such outputs 40, 42 from the classifiers are inconclusive and appear to conflict with each other, the output communication provided to the subject may indicate that that the subject should proceed with caution. One example of such an output communication is a yellow light. This output corresponds to the first row 52 of the truth table 50 of FIG. 12.

At Time 2, the output 40 from the contra-ictal classifier is high (H) and the output from the pro-ictal classifier 42 is low (L). Such a classification indicates that there is a low likelihood that the subject has an increased susceptibility for a seizure and a high likelihood of being in a contra-ictal state. These classifiers appear to be consistent with each other; consequently, the output communication provided to the subject may indicate that the subject is in a contra-ictal state. One example of such an output communication is the display of a green light. This scenario corresponds to the second row 54 of FIG. 12.

As shown in FIG. 11, the green light would stay on until Time 3 where the output 40 from the contra-ictal classifier is trending lower but is still above threshold 44 (is high (H)) and the output 42 from the pro-ictal classifiers transitions to high (H). As shown in the third row 56 of the truth table of FIG. 12, when both classifier outputs are high (H)—which indicates a high likelihood that the subject is at an increased susceptibility to a seizure and a high likelihood that the subject is in a contra-ictal condition (inconsistent outputs)— an output communication is output to the patent to indicate that they should proceed with caution (e.g., yellow light).

Finally, at Time 4 in FIG. 11, the output 40 from the contra-ictal classifier has fully transitioned to low (L) (e.g., low likelihood that the subject is in a contra-ictal state) and the output 42 from the pro-ictal classifier is above threshold 44 and is high (H) (e.g., high likelihood that the subject is at an increased susceptibility to a seizure). This scenario corresponds with the fourth row 58 of FIG. 12 and the red light would be output to the subject—which indicates that the subject has a high susceptibility to a seizure and should take an appropriate action.

In another embodiment shown in FIG. 11, different thresholds are used for the contra-ictal and pro-ictal classifiers. For example, the contra-ictal classifier output 40 could be compared to a higher threshold 43, while the pro-ictal classifier output 42 could be compared to the lower threshold 44. In this example, the contra-ictal indication (e.g., green light) might be provided if the contra-ictal classifier output 40 exceeds the threshold 43 and if the pro-ictal classifier output 42 does not exceed the threshold 44; the pro-ictal indication (e.g., red light) might be provided if the contra-ictal classifier output 40 does not exceed threshold 43 and if the pro-ictal classifier output 42 exceeds threshold 44; and an indication that the outputs are inconclusive (e.g., a yellow light) if neither classifier output exceeds its threshold.

While FIGS. 11 and 12 illustrate the use of two one-class classifiers, any number and type of classifier may be used by the systems of the present invention. For example, in other embodiments it may be desirable to have a single classifier classify the subject as being in one of three conditions—an inter-ictal class, a pro-ictal class, and a contra-ictal class— which could correspond, respectively, to a normal propensity for a future seizure, an elevated or high propensity for a future seizure, and a low propensity for a future seizure.

In other embodiments, the output of the classification algorithm would indicate the existence of a contra-ictal condition (e.g., a green light) so long as the extracted feature vector corresponds only with training points that almost never preceded a seizure by less than the predetermined time period, such as 90 minutes. The output of the classification algorithm would indicate the existence of a pro-ictal condition (e.g., a red light) if the extracted feature corresponds to a region of the feature space indicative of pro-ictal state. This indication is not a seizure prediction; a pro-ictal condition might resolve without a seizure ever occurring. The end of a contra-ictal indication does indicate, however, that it is no longer unlikely that a seizure will occur within 90 minutes (or other predetermined time). In addition, in these embodiments, while the contra-ictal indication has a predetermined time associate with it, the pro-ictal indication does not. The subject may stay in a pro-ictal state for a prolonged period of time, or the subject might leave the pro-ictal state immediately after entering it.

In still other embodiments, the classification algorithm for a contra-ictal indication can be derived by determining the kinds of feature vectors that never preceded a pro-ictal condition by less than a predetermined time. When trained using this kind of patient data, this contra-ictal classification algorithm would indicate a contra-ictal condition (such as be lighting a green light) when a feature vector extracted from a patient's physiological signal (such as an EEG) corresponds to one of such feature vectors, thereby indicating that the patient is unlikely to transition to a pro-ictal state within that predetermined time period.

In yet other embodiments, the contra-ictal indication classification algorithm can be derived by determining the kinds of features that never preceded a pro-ictal condition by less than a predetermined time and never preceded a seizure by less than the predetermined time. When trained using this kind of patient data, this contra-ictal classification algorithm would indicate a contra-ictal condition (such as be lighting a green light) when a feature extracted from a patient's physiological signal (such as an EEG) corresponds to one of such features, thereby indicating that the patient is unlikely to transition to either a pro-ictal state or to a seizure within that predetermined time period.

Figure 13:
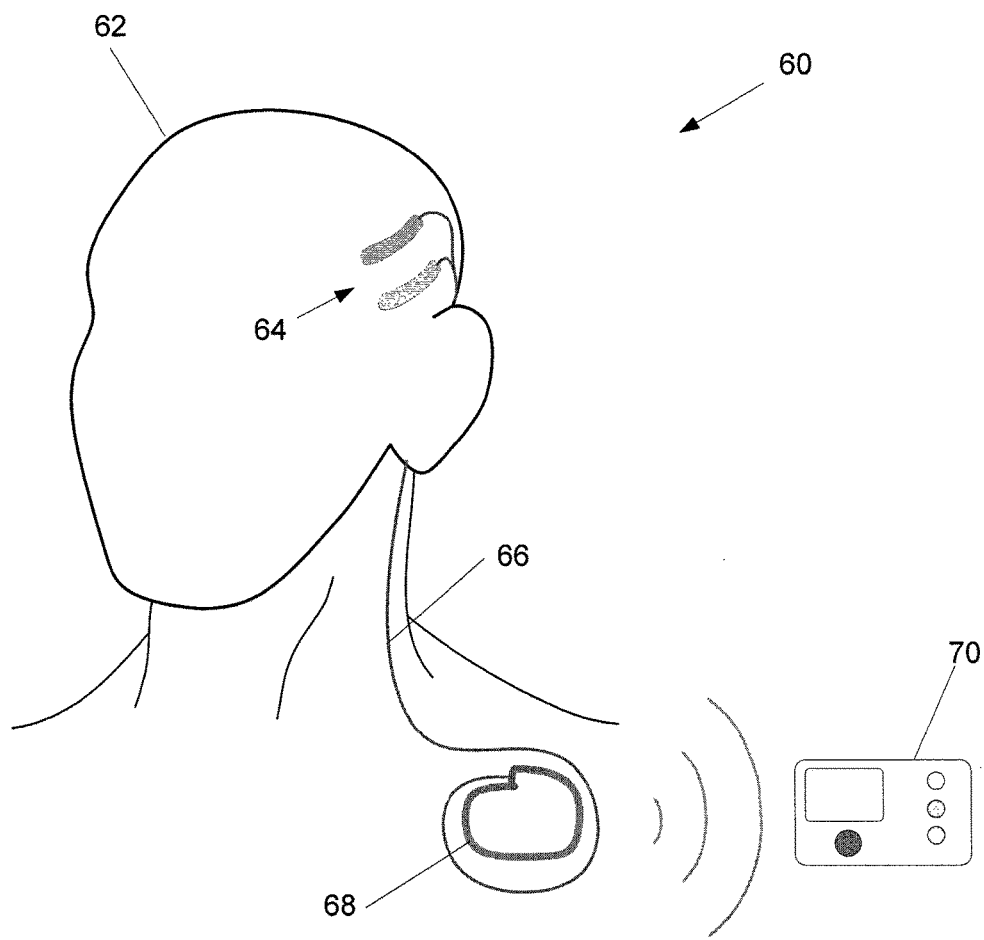
FIG. 13 is a simplified system that may encompass the algorithms of FIG. 2.

FIG. 13 illustrates one example of a system in which the algorithms 19, 20 (FIG. 2) of the present invention may be embodied. The system 60 is used to monitor a neurological condition of subject 62 for purposes of estimating a subject's susceptibility for a neurological event. The system 60 of the illustrated embodiment provides for substantially continuous sampling and analysis of brain wave electrical signals.

The system 60 comprises one or more sensors 64 configured to measure signals from the subject 62. The sensors 64 may be located anywhere in or on the subject. In the exemplary embodiment, the sensors 64 are configured in one or more arrays and are positioned to sample electrical activity from the subject's brain. The sensors 64 may be attached to the surface of the subject's body (e.g., scalp electrodes), attached to the skull (e.g., subcutaneous electrodes, bone screw electrodes, sphenoidal electrodes, and the like), or, may be implanted intracranially in the subject 62. In some embodiments, one or more of the sensors 64 will be implanted either 1) adjacent a previously identified epileptic focus, a portion of the brain where such a focus is believed to be located, 2) adjacent a portion of a seizure network, 3) substantially opposite the previously identified epileptic focus, or 4) any combination thereof.

Any number of sensors 64 may be employed, but the sensors 64 will preferably include between 1 sensor and 64 sensors. The sensors may take a variety of forms. In one embodiment, the sensors comprise grid electrodes, strip electrodes and/or depth electrodes which may be permanently implanted through burr holes in the head. In addition to measuring brain activity, other sensors (not shown) may be employed to measure other physiological signals from the subject 62.

In an embodiment, the sensors 64 will be configured to substantially continuously sample the brain activity in the immediate vicinity of the sensors 64. The sensors could be one or more microelectrodes that are configured to sense the activity of a single neuron, or the sensors could be macroelectrodes that are configured to sense activity of a group of neurons in the subject's brain. The sensors 64 are electrically joined via cables 66 to a communication unit 68, but could be wirelessly coupled to the communication unit or other external device. In one embodiment, the cables 66 and communication unit 68 will be implanted in the subject 62. For example, the communication unit 68 may be implanted in a sub-clavicular cavity of the subject 22. In alternative embodiments, the cables 66 and communication unit 68 may be implanted in other portions of the subject's body (e.g., in the head) or attached to the subject 62 externally.

The communication unit 68 is configured to facilitate the sampling of signals from the sensors 64. Sampling of brain activity is typically carried out at a rate above about 200 Hz, and preferably between about 200 Hz and about 1000 Hz, and most preferably at or above about 400 Hz. The sampling rates could be higher or lower, depending on the specific features being monitored, the subject 62, and other factors. Each sample of the subject's brain activity is typically encoded using between about 8 bits per sample and about 32 bits per sample, and preferably about 16 bits per sample. In alternative embodiments, the communication unit 68 may be configured to measure the signals on a non-continuous basis. In such embodiments, signals may be measured periodically or aperiodically.

An external data device 70 is preferably carried external to the body of the subject 22. The external data device 70 receives and stores signals, including measured EEG signals and possibly other physiological signals, from the communication unit 68. External data device 70 could also receive and store extracted features, classifier outputs, subject inputs, and the like. Communication between the external data device 70 and the communication unit 68 may be carried out through wireless communication, such as a radiofrequency link, infrared link, optical link, ultrasonic link, or other conventional or proprietary wireless link. The wireless communication link between the external data device 70 and the communication unit 68 may provide a one-way or two-way communication link for transmitting data. In alternative embodiments, it may be desirable to have a direct communications link from the external data device 70 to the communication unit 68, such as, for example, via an interface device positioned below the subject's skin. The interface (not shown) may take the form of a magnetically attached transducer that would enable power to be continuously delivered to the communication unit 68 and would provide for relatively higher rates of data transmission. Error detection and correction methods may be used to help insure the integrity of transmitted data. If desired, the wireless data signals can be encrypted prior to transmission to the external data device 70.

Figure 14:
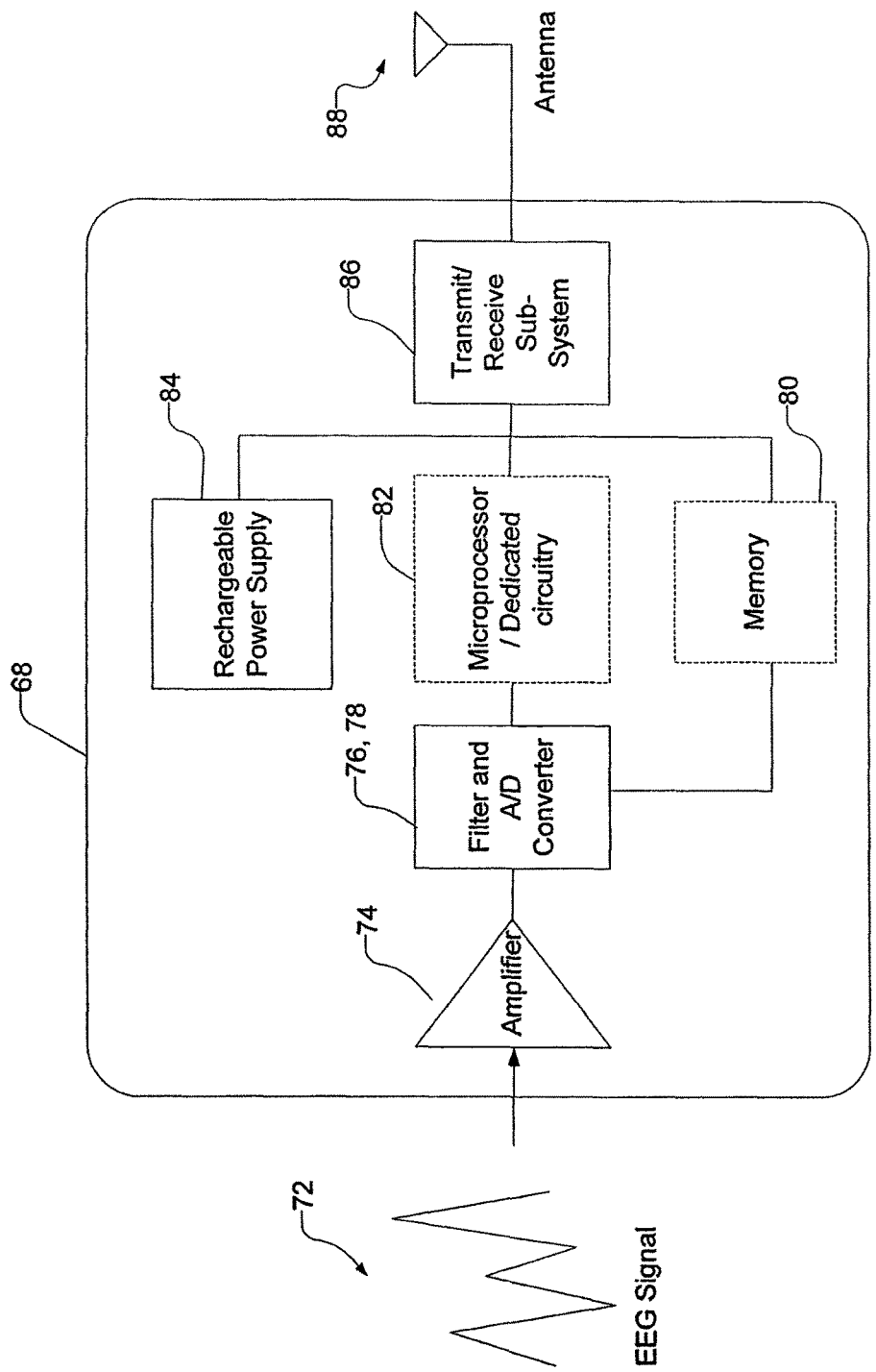
FIG. 14 illustrates one embodiment of an implanted communication device.

FIG. 14 depicts a block diagram of one embodiment of a communication unit 68 that may be used with the systems and methods described herein. Signals 72 from the sensors 64 are received by the communication unit 68. The signals may be initially conditioned by an amplifier 74, a filter 76, and an analog-to-digital converter 78. A memory module 80 may be provided for storage of some of the sampled signals prior to transmission via a transmit/receive subsystem 86 and antenna 88 to the external data device 70. For example, the memory module 80 may be used as a buffer to temporarily store the conditioned signals from the sensors 64 if there are problems with transmitting data to the external data device 70, such as may occur if the external data device 70 experiences power problems or is out of range of the implanted communication unit 68. The external data device 70 can be configured to communicate a warning signal to the subject in the case of data transmission problems to inform the subject and allow him or her to correct the problem.

Energy for the system may be supplied by a non-rechargeable or rechargeable power supply 84. The power supply may be a battery, or the like. The rechargeable power supply 84 may also be in communication with a transmit/receive subsystem 86 so as to receive power from outside the body by inductive coupling, radiofrequency (RF) coupling, and the like. Power supply 84 will generally be used to provide power to the other components of the implantable device.

The communication unit 68 may optionally comprise circuitry of a digital or analog or combined digital/analog nature and/or a microprocessor (such as a multiple core microprocessor manufactured by Intel Corporation or Advanced Micro Devices Inc. (AMD)), referred to herein collectively as "microprocessor" 82, for processing the signals prior to transmission to the external data device 70. The microprocessor 82 may execute at least portions of the analysis as described herein. For example, in some configurations, the microprocessor 82 may run one or more feature extractors 14a, 14b, 15 (FIG. 2) that extract characteristics of the measured signal that are relevant to the purpose of monitoring. Thus, if the system is being used for diagnosing or monitoring epileptic subjects, the extracted characteristics (either alone or in combination with other characteristics) may be indicative of the subject's susceptibility to or protection from a neurological event (e.g., pro-ictal or contra-ictal). Once the characteristic(s) are extracted, the microprocessor 82 may facilitate the transmission of the extracted characteristic(s) to the external data device 70 and/or store the extracted characteristic(s) in memory 80. Because the transmission of the extracted characteristics is likely to include less data than the measured signal itself, such a configuration will likely reduce the bandwidth requirements for the communication link between the communication unit 68 and the external data device 70.

In some configurations, the microprocessor 82 in the communication unit 68 may run one or more classifiers 16, 17 (FIG. 2) as described above with respect to FIG. 2. The result 18 (FIG. 2) of the classification may be communicated to the external data device 70. In such embodiments, the external data device 70 will primarily act as a data storage device and user interface to the subject.

While the external data device 70 may include any combination of conventional components, FIG. 15 provides a schematic diagram of some of the components that may be included. Signals from the communication unit 68 are received at an antenna 90 and conveyed to a transmit/receive subsystem 92. The signals received may include, for example, a raw measured EEG signal, a processed measured signal, extracted characteristics from the measured EEG signal, a result from analysis software that ran on the implanted microprocessor 82, or any combination thereof.

The received data may thereafter be stored in memory 94, such as a hard drive, RAM, EEPROM, removable flash memory, or the like and/or processed by a microprocessor (such as a multiple core microprocessor manufactured by Intel Corporation or Advanced Micro Devices Inc. (AMD)), application specific integrated circuit (ASIC) or other dedicated circuitry of a digital or analog or combined digital/analog nature, referred to herein collectively as a "microprocessor" 96. Microprocessor 96 may be configured to request that the communication unit 68 perform various checks (e.g., sensor impedance checks) or calibrations prior to signal recording and/or at specified times to ensure the proper functioning of the system.

Data may be transmitted from memory 94 to microprocessor 96 where the data may optionally undergo additional processing. For example, if the transmitted data is encrypted, it may be decrypted. The microprocessor 96 may also comprise one or more filters that filter out low-frequency or high-frequency artifacts (e.g., muscle movement artifacts, eye-blink artifacts, chewing, and the like) so as to prevent contamination of the measured signals.

External data device 70 will typically include a user interface 100 for displaying outputs to the subject and for receiving inputs from the subject. The user interface will typically comprise outputs such as auditory devices (e.g., speakers) visual devices (e.g., LCD display, LEDs), tactile devices (e.g., vibratory mechanisms), or the like, and inputs, such as a plurality of buttons, a touch screen, and/or a scroll wheel.

The user interface may be adapted to allow the subject to indicate and record certain events. For example, the subject may indicate that medication has been taken, the dosage, the type of medication, meal intake, sleep, drowsiness, occurrence of an aura, occurrence of a neurological event, or the like. Such inputs may be used in conjunction with the measured data to improve the analysis.

The LCD display may be used to output a variety of different communications to the subject including, status of the device (e.g., memory capacity remaining), battery state of one or more components of system, whether or not the external data device 70 is within communication range of the communication unit 68, subject's condition (e.g., a neurological event warning or safety indication), a prediction (e.g., a neurological event prediction), a recommendation (e.g., "take medicine"), or the like. It may be desirable to provide an audio output or vibratory output to the subject in addition to or as an alternative to the visual display on the LCD.

As noted above and illustrated in FIG. 15, the external data device 70 may comprise a plurality of LEDs to provide a substantially continuous, real-time indication to the subject of their condition. In the illustrated embodiment, the LEDs may include three LEDs—a green LED, a yellow LED, and a red LED. While not shown, it may also be desirable to provide additional LEDs of different colors or additional LEDs in each color to indicate a graded condition. As stated above, the period of time associated with a contra-ictal state can be a predetermined time period. There can also be multiple predetermined periods of varying duration. The external device could therefore comprise a plurality of outputs which indicate one of the multiple predetermined contra-ictal periods of time. For example, it may be desirable to illuminate two or more green lights when the subject is in a condition that is determined to be even more unlikely to experience a seizure. More specifically, one green light illuminated could indicate a contra-ictal period duration of 10 minutes, whereas two green lights illuminated could indicate a contra-ictal period of 20 minutes. Or a slowly blinking green light could indicate a longer contra-ictal period than a rapidly blinking green light. On the other extreme, but similarly, it may be desirable to provide, and illuminate, two or more red lights when a seizure is detected or is imminent.

External data device 70 may also include a power source 102 or other conventional power supply that is in communication with at least one other component of external data device 70. The power source 102 may be rechargeable. If the power source 102 is rechargeable, the power source may optionally have an interface for communication with a charger 104. While not shown in FIG. 15, external data device 70 will typically comprise a clock circuit (e.g., oscillator and frequency synthesizer) to provide the time base for synchronizing the external data device 70 and the communication unit 68.

Referring again to FIG. 14, in a preferred embodiment, most or all of the processing of the signals received by the communication unit 68 is done in an external data device 70 that is external to the subject's body. In such embodiments, the communication unit 68 would receive the signals from subject and may or may not pre-process the signals and transcutaneously transmit a signal that is indicative of at least some aspect of some or all of the measured signals to external data device 70, where the measurement of the susceptibility to the neurological event and possible therapy determination is made Advantageously, such embodiments reduce the amount of computational processing power that needs to be implanted in the subject, thus potentially reducing energy consumption and increasing battery life. Furthermore, by having the processing external to the subject, the judgment or decision making components of the system may be more easily reprogrammed or custom tailored to the subject without having to reprogram the implanted communication unit 68.

The EEG analysis systems of the present invention, however, may be embodied in a device that is implanted in the subject's body, external to the subject's body, or a combination thereof. For example, in one embodiment the algorithm system may be fully stored in and processed by the communication unit 68 that is implanted in the subject's body. In such embodiments, the subject's propensity for neurological event characterization (or whatever output is generated by the classifiers) is calculated in the implanted communication unit 68 and a data signal is transmitted to the external subject communication assembly. The external processor performs any remaining processing to generate and provide the communication output to the subject. Such embodiments have the benefit of maintaining processing within the subject, while reducing the communications demands on the communication unit 68.

In other embodiments, the signals 72 may be partially processed in the communication unit 68 before transmitting data to the external data device 70 so as to reduce the total amount of data to be transmitted, thereby reducing the power demands of the transmit/receive subsystem 86. Examples include: digitally compressing the signals before transmitting them; selecting only a subset of the measured signals for transmission; selecting a limited segment of time and transmitting signals only from that time segment; extracting salient characteristics of the signals, transmitting data representative of those characteristics rather than the signals themselves, and transmitting only the result of classification. Further processing and analysis of the transmitted data may take place in the external data device 70.

In yet other embodiments, it may be possible to perform some of the signal processing in the communication unit 68 and some of the signal processing in the external data device 70. For example, one or more characteristics from the one or more signals may be extracted with feature extractors in the communication unit 68. Some or all of the extracted characteristics may be transmitted to the external data device 70 where the characteristics may be classified to assess the subject's susceptibility for a neurological event. If desired, external data device 70 may be tailored to the individual subject. Consequently, the classifier may be adapted to allow for transmission or receipt of only the characteristics from the communication unit 68 that are useful for that individual subject. Advantageously, by performing feature extraction in the communication unit 68 and classification in an external device at least two benefits may be realized. First, the amount of wireless data transmitted from the communication unit 68 to the external data device 70 is reduced (versus transmitting pre-processed data). Second, classification, which embodies the decision or judgment component, may be easily reprogrammed or custom tailored to the subject without having to reprogram the communication unit 68.

In yet another embodiment, feature extraction may be performed external to the body. Pre-processed signals (e.g., filtered, amplified, converted to digital) may be transcutaneously transmitted from communication unit 68 to the external data device 70 where one or more characteristics are extracted from the one or more signals with feature extractors. Some or all of the extracted characteristics may be transcutaneously transmitted back into the communication unit 68, where a second stage of processing may be performed on the characteristics, such as classifying of the characteristics (and other signals) to characterize the subject's propensity for the onset of a future neurological event. If desired, to improve bandwidth, the classifier may be adapted to allow for transmission or receipt of only the characteristics from the subject communication assembly that are predictive for that individual subject. Advantageously, because feature extractors may be computationally expensive and energy hungry, it may be desirable to have the feature extractors external to the body, where it is easier to provide more processing and larger power sources.

Other details of devices useful for practicing the invention may be found in co-owned U.S. patent application Ser. No. 12/020,507, concurrently filed on Jan. 25, 2008, titled "METHODS AND SYSTEMS FOR MEASURING A PATIENT'S SUSCEPTIBILITY TO A SEIZURE," to Leyde et al., the disclosure of which is incorporated herein by reference.

One particular advantage of the present invention is the ability to provide a substantially continuous, substantially real-time indication to the subject of their neurological condition. The ability to inform the subject that they are unlikely to transition to an ictal condition within a period of time will reduce the uncertainty that effects every aspect of their day to day life and opens up the possibility for the subject to perform tasks that most people take for granted.

Such a system would further enable use of novel therapies to prevent the occurrence of the neurological event. Therapies include automatic or manual delivery of anti-epileptic drugs, vagus nerve stimulation, brain stimulation, etc. Some potential therapies are described in commonly owned U.S. Pat. No. 7,231,254, application No. Ser. No. 10/889,844, filed Jul. 12, 2004 to DiLorenzo, and pending U.S. patent application Ser. No. 11/321,898, filed Dec. 28, 2005 to Leyde et al., the complete disclosure of which is incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of identifying a contra-ictal status of a subject, the method comprising:
    obtaining, by one or more physiological sensors, an electroencephalogram (EEG) signal dataset from the subject;
    using a processor to complete steps of:
        generating an N-dimensional feature vector for each of different time points of the EEG signal dataset;
        identifying a grouping of contra-ictal feature vectors that is substantially free of pro-ictal feature vectors, wherein the contra-ictal feature vectors are associated with a low susceptibility of having a seizure and the pro-ictal feature vectors are associated with high susceptibility of having a seizure;
        identifying a grouping of pro-ictal feature vectors that is substantially free of contra-ictal feature vectors;
        using the grouping of contra-ictal feature vectors to provide an output associated with a contra-ictal status and using the grouping of pro-ictal feature vectors to provide an output associated with a pro-ictal status;
        comparing the contra-ictal output to at least one threshold to determine a contra-ictal state;
        comparing the pro-ictal output to at least one threshold to determine a pro-ictal state;
        selecting an indicator from among at least three indicators based on the contra-ictal state and the pro-ictal state, each of the at least three indicators corresponding to a different susceptibility of having a seizure, wherein the selected indicator indicates whether the subject has the contra-ictal status; and
    displaying, by a seizure advisory system, the selected indicator.

2. The method of claim 1 further comprising storing the identified grouping of contra-ictal feature vectors or a mathematical representation of the identified grouping of contra-ictal feature vectors in memory.

3. The method of claim 1 further comprising customizing a contra-ictal algorithm for the subject based on the N-dimensional feature vector and the processor using the customized contra-ictal algorithm.

4. The method of claim 1, wherein the displaying of the indicator includes a report that a seizure is unlikely to occur for a time period.

5. The method of claim 4, wherein the time period is at least one of 5 minutes, 10 minutes, 15 minutes, 20 minutes, 30 minutes, 60 minutes, 90 minutes, greater than 5 minutes, greater than 15 minutes, greater than 30 minutes, greater than 60 minutes, and greater than 90 minutes.

6. The method of claim 1, wherein the indicator is the identification of the contra-ictal status of the subject and corresponds to a time period that the subject is estimated to remain in the contra-ictal status.

7. The method of claim 6, wherein the time period is at least one of 5 minutes, 10 minutes, 15 minutes, 20 minutes, 30 minutes, 60 minutes, 90 minutes, greater than 5 minutes, greater than 15 minutes, greater than 30 minutes, greater than 60 minutes, and greater than 90 minutes.

8. The method of claim 1, wherein selecting the indicator comprises:
    selecting a first indicator of the at least three indicators in response to the contra-ictal output being above at least one threshold and the pro-ictal output being below at least one threshold, the first indicator corresponding to a low susceptibility of having a seizure;
    selecting a second indicator of the at least three indicators in response to the contra-ictal output being below at least one threshold and the pro-ictal output being above at least one threshold, the second indicator corresponding to a high susceptibility of having a seizure;
    selecting a third indicator of the at least three indicators in response to the contra-ictal output being below at least one threshold and the pro-ictal output being below at least one threshold, the third indicator corresponding to neither the contra-ictal state nor the pro-ictal state; and
    selecting the third indicator of the at least three indicators in response to the contra-ictal output being above at least one threshold and the pro-ictal output being above at least one threshold.

9. The method of claim 8, wherein the first indicator is a green light, the second indicator is a red light, and the third indicator is a yellow light.

10. A method of identifying a contra-ictal status of a subject, the method comprising:
    obtaining, by one or more physiological sensors, an electroencephalogram (EEG) signal dataset from the subject, the EEG signal dataset including contra-ictal data corresponding to a contra-ictal status of the subject in which the subject has a low susceptibility of having a seizure for a time period, the EEG signal dataset further including pro-ictal data corresponding to a pro-ictal status of the subject in which the subject has a high susceptibility of having a seizure;
    using a processor to complete steps of:
        distinguishing the contra-ictal data from the pro-ictal data within the EEG signal dataset;

providing an output associated with the contra-ictal status and providing an output associated with the pro-ictal status based on the distinguished data;

comparing the contra-ictal output to at least one threshold to determine a contra-ictal state;

comparing the pro-ictal output to at least one threshold to determine a pro-ictal state;

selecting an indicator from among at least three indicators based on the contra-ictal state and the pro-ictal state, each of the at least three indicators corresponding to a different susceptibility of having a seizure, wherein the selected indicator indicates whether the subject has the contra-ictal status;

displaying, by a seizure advisory system, the selected indicator; and reporting, by the processor, the contra-ictal status of the subject.

11. The method of claim 10, wherein the time period is at least one of 5 minutes, 10 minutes, 15 minutes, 20 minutes, 30 minutes, 60 minutes, 90 minutes, greater than 5 minutes, greater than 15 minutes, greater than 30 minutes, greater than 60 minutes, and greater than 90 minutes.

12. The method of claim 10, wherein the reporting is to the subject or a care provider of the subject.

13. The method of claim 10, wherein the reporting includes reporting the time period.

14. The method of claim 13, wherein the time period is at least one of 5 minutes, 10 minutes, 15 minutes, 20 minutes, 30 minutes, 60 minutes, 90 minutes, greater than 5 minutes, greater than 15 minutes, greater than 30 minutes, greater than 60 minutes, and greater than 90 minutes.

15. The method of claim 10, further comprising:
providing a therapeutic response to the subject.

16. A method of identifying a contra-ictal status of a subject, the method comprising:

obtaining, by one or more physiological sensors, an electroencephalogram (EEG) signal dataset from the subject, the EEG signal dataset corresponding to a normal non-seizure status of the subject;

using a processor to complete steps of:

distinguishing contra-ictal data from pro-ictal data within the EEG signal dataset, wherein the contra-ictal data is associated with a low susceptibility of having a seizure and the pro-ictal data is associated with a high susceptibility of having a seizure;

in response to distinguishing the contra-ictal data from the pro-ictal data, providing an output associated with a contra-ictal status for a time period and providing an output associated with a pro-ictal status for the time period, the time period being a future period of time;

comparing the contra-ictal output to at least one threshold to determine a contra-ictal state for the time period;

comparing the pro-ictal output to at least one threshold to determine a pro-ictal state for the time period;

selecting an indicator from among at least three indicators based on the contra-ictal state and the pro-ictal state, each of the at least three indicators corresponding to a different susceptibility of having a seizure for the time period, wherein the selected indicator indicates whether the subject has the contra-ictal status; and displaying, by a seizure advisory system, the selected indicator.

17. The method of claim 16, wherein the time period is at least one of 5 minutes, 10 minutes, 15 minutes, 20 minutes, 30 minutes, 60 minutes, 90 minutes, greater than 5 minutes, greater than 15 minutes, greater than 30 minutes, greater than 60 minutes, and greater than 90 minutes.

18. The method of claim 16, further comprising:
providing a therapeutic response to the subject.

* * * * *